(12) United States Patent
Meister et al.

(10) Patent No.: US 12,097,033 B2
(45) Date of Patent: Sep. 24, 2024

(54) METHODS AND SYSTEMS FOR ELECTRODE POOLING

(71) Applicant: California Institute of Technology, Pasadena, CA (US)

(72) Inventors: Markus Meister, Pasadena, CA (US); Kyu Hyun Lee, San Francisco, CA (US); Yu-Li Ni, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 957 days.

(21) Appl. No.: 17/104,902

(22) Filed: Nov. 25, 2020

(65) Prior Publication Data

US 2021/0153798 A1 May 27, 2021

Related U.S. Application Data

(60) Provisional application No. 62/940,142, filed on Nov. 25, 2019.

(51) Int. Cl.
*A61B 5/273* (2021.01)
*A61B 5/00* (2006.01)
*A61B 5/304* (2021.01)

(52) U.S. Cl.
CPC .............. *A61B 5/273* (2021.01); *A61B 5/304* (2021.01); *A61B 5/7217* (2013.01)

(58) Field of Classification Search
CPC ........ A61B 5/273; A61B 5/304; A61B 5/7217
See application file for complete search history.

(56) References Cited

U.S. PATENT DOCUMENTS

2005/0203366 A1* 9/2005 Donoghue ........... A61B 5/6814
607/46
2010/0317983 A1* 12/2010 Vajdic ................... A61B 5/366
600/512

OTHER PUBLICATIONS

Marie Engelene J. Obien, et al., "Revelaing neuronal functionl through microelectrode array recordings", Jan. 6, 2015, frontiers in Neuroscience, pp. 1-30 (Year: 2015).*
James J. Jun, et al., "Fully integrated silicon probes for high-density recording of neural activity", Nov. 9, 2017, Letter Research (Year: 2017).*
George Dimitriadis, et al., "Why not record from every channel with a CMOS scanning probe?", Mar. 7, 2018 (Year: 2018).*

* cited by examiner

*Primary Examiner* — Adam Z Minchella
(74) *Attorney, Agent, or Firm* — Kilpatrick Townsend & Stockton LLP

(57) ABSTRACT

A method includes providing a first electrode and a second electrode, receiving a first plurality of signals from the first electrode during a first period of time, and receiving a second plurality of signals from the second electrode during a second period of time. The method also includes receiving a pooled signal comprising a third plurality of signals from the first electrode and a fourth plurality of signals from the second electrode and isolating, from the pooled signal, one or more of the third plurality of signals and one or more of the fourth plurality of signals.

25 Claims, 11 Drawing Sheets

METHODS AND SYSTEMS FOR ELECTRODE POOLING

CROSS-REFERENCES TO RELATED APPLICATIONS

This application claims priority to U.S. Provisional Patent Application No. 62/940,142, filed on Nov. 25, 2019, which is hereby incorporated by reference in its entirety for all purposes.

BACKGROUND OF THE INVENTION

Silicon probes that record electrical signals from neurons include hundreds of electrodes, each configured to propagate the electrical signal of the neuron to a receiver. The placement of silicon probes must be precisely positioned within the brain to obtain signals from neurons of interest. Due to volume limitation within the brain, silicon probes may be designed with fewer wires than electrodes. As a result, the silicon probe may be limited in the number of channels that can be recorded simultaneously, which may reduce the ability of the silicon probe to record neural activity.

SUMMARY OF THE INVENTION

Embodiments of the present invention generally relate to pooling electrodes, and more particularly, to connecting multiple electrodes to a receiver unit using a single lead.

Embodiments of the present invention utilize electrode pooling, which, as described more fully herein, uses a single lead, also referred to as a wire, to serve multiple recording sites through a set of controllable switches. The inventors have demonstrated electrode pooling using an electrode array and characterized the effect of electrode pooling on signal and noise. Therefore, in contrast with conventional techniques of performing neural recording, embodiments of the present invention enhance the number of neurons recorded using a reduced number of leads.

According to an embodiment of the present invention, a method is provided. The method includes executing, by a receiver unit, a sample phase for a plurality of electrodes, each electrode of the plurality of electrodes being connected to a switching unit, the switching unit being connected to the receiver unit via a first lead. The switching unit is configured to connect one or more electrodes to the receiver unit via the first lead. The sampling phase includes, for each electrode of the plurality of electrodes, receiving, at the receiver unit, a plurality of signals from the electrode while the electrode is connected to the receiver unit via the first lead. Other electrodes of the plurality of electrodes are not connected to the receiver unit via the first lead. The sampling phase also includes, for each electrode of the plurality of electrodes, identifying, from the plurality of signals, a noise value for the electrode, and assigning, based on the plurality of signals and the noise value, the electrode to an electrode pool that includes two or more electrodes. The method also includes executing, by the receiver unit, an acquisition phase that includes, connecting, by the switching unit, the two or more electrodes of the electrode pool to the receiver unit at a same time via the first lead, receiving, by the receiver unit from the electrode pool, a pooled signal, the pooled signal being a combination of the signals generated by the two or more electrodes of the electrode pool, and isolating, from the pooled signal and based on the plurality of signals of each electrode of the electrode pool, signals associated with one or more of the electrodes in the electrode pool.

According to another embodiment of the present invention, a method is provided that includes providing a first electrode and a second electrode, receiving a first plurality of signals from the first electrode during a first period of time, and receiving a second plurality of signals from the second electrode during a second period of time. The method also includes receiving a pooled signal comprising a third plurality of signals from the first electrode and a fourth plurality of signals from the second electrode and isolating, from the pooled signal, one or more of the third plurality of signals and one or more of the fourth plurality of signals.

According to a particular embodiment of the present invention, a method is provided that includes providing a first electrode and a second electrode and sampling signals from the first electrode to detect a characteristic of the first electrode and a noise value for the first electrode. The method also includes sampling signals from the second electrode to detect a characteristic of the second electrode and a noise value for the second electrode. The method also includes generating an electrode pool that includes the first electrode and the second electrode based on the characteristic of the first electrode, the noise value for the first electrode, the characteristic of the second electrode, and the noise value for the second electrode. Signals received from the electrode pool correspond to a combination of signals from the first electrode and the second electrode.

Another aspect of the present disclosure includes a system comprising one or more processors and a non-transitory, computer-readable medium storing instructions, which, when executed by one or more processors, cause the one or more processors to perform the method described above.

Another aspect of the present disclosure includes non-transitory, computer-readable medium storing instructions, which, when executed by one or more processors, cause one or more processors to perform the method described above.

Numerous benefits are achieved by way of the various embodiments over conventional techniques. For example, the various embodiments provide methods and systems for connecting multiple electrodes to a receiver unit using a single lead. Electrode pooling can increase a quantity of electrodes per lead, thereby increasing the sensing resolution. For space-limited applications, such as deep brain recording and/or stimulation, electrode pooling allows for a substantial reduction in size, wiring, and wiring complexity of the electrode unit, which reduces the impact of the sensing unit in the space-limited environment. These and other embodiments, along with many of their advantages and features, are described in more detail in conjunction with the text below and attached figures.

BRIEF DESCRIPTION OF THE DRAWINGS

Aspects and features of the various embodiments will be more apparent by describing examples with reference to the accompanying drawings, in which.

DETAILED DESCRIPTION OF THE INVENTION

Figure 1:
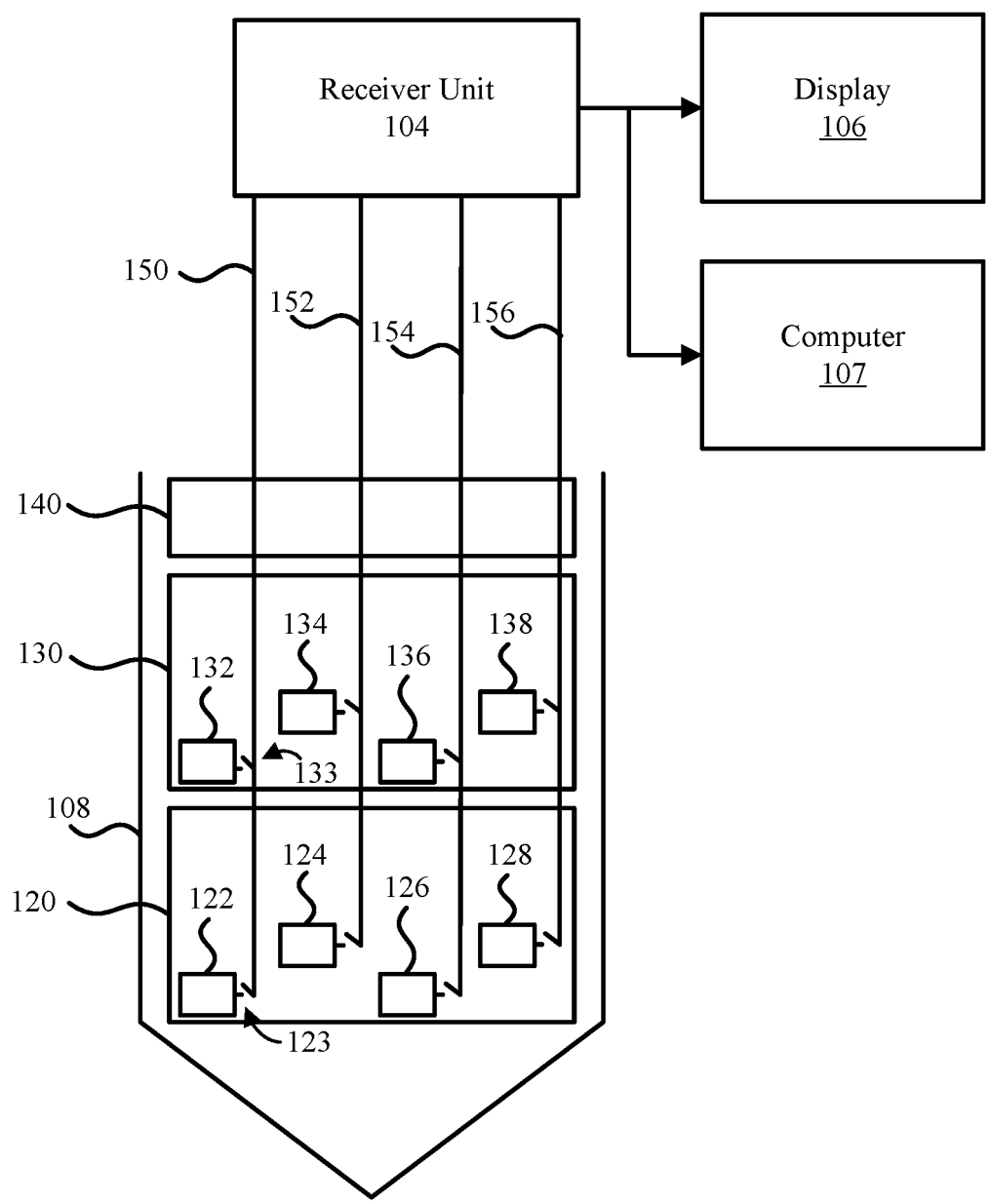
FIG. 1 is a diagram illustrating an electrode pooling system according to some aspects of the present disclosure.

According to embodiments of the present invention, probes are provided that include a greater number of electrodes than leads (e.g., to reduce the size and impact of the probe in space-limited environments). The probe includes a set of switches that may be operated to establish a connection between an electrode and a lead, which is connected to a receiver. During a sampling phase, the probe is operated such that the receiver receives signals from only one electrode per lead at a time, enabling the receiver to characterize the signals associated with the particular electrode. Then, in an acquisition phase, the switches may be operated to connect multiple electrodes to a single lead, thereby receiving signals from the multiple electrodes as a pooled signal. By extracting signals associated with particular electrodes from the pooled signal, embodiments of the present invention enable improved neural analysis efficiency by measuring multiple neurons using a reduced number of leads.

Probes for use in the brain may be used to capture electrical signals generated from neurons. An average neuron may fire (e.g., produce a measurable potential) roughly 10 times a second with each action potential lasting for around 1 ms. Therefore, the neuron's signal occupies less than 1% of the time axis in an extracellular recording. The neuron firing may be represented as a spike in the waveform measured at an electrode. These spikes can be referred to as neural signals. Since neurons do not fire frequently, signals from electrodes that monitor a neuron may be sparse waveforms in which most of the waveform is not related to neuron activity. The sparsity of the waveform is utilized by embodiments of the present invention and leveraged by pooling electrodes on a same lead. The pooled signal (e.g., the signals of each electrode of the electrode pool being received concurrently) may include neural signals from the neurons monitored by each electrode. Since the neurons do not fire frequently, the neural signals from one electrode are unlikely to overlap. The characteristics of the neural signals from each electrode may be identified and used to determine which neural signals of the pooled signal were received from which electrodes. Thus, using embodiments of the present invention, multiple neural signals may be transmitted on a common lead and separated for analysis and the electrode associated with each signal can be determined, which can then be correlated with particular neurons.

Methods and systems are disclosed herein for establishing and using electrode pools. Electrode pools may be established to connect two or more electrodes of a probe to a receiver via a same lead. Since the probe is no longer bound by the one-to-one relationship between lead and electrode, the quantity of simultaneous channels of the probe may be increased without significantly impacting the received signals.

Establishing electrode pools may include a sampling phase and an acquisition phase, which can also be referred to as a pooled phase. During the sampling phase, signals from each electrode may be consecutively sampled to identify one or more characteristics of the signals associated with each electrode. For instance, the characteristics, which may also be referred to as a signature, may correspond to a particular feature of a waveform received from the electrode such as a spike in magnitude (e.g., from a neuron firing). Statistics associated with the signals from each electrode can be analyzed and characteristics of the signals can be extracted. The characteristic may correspond to the shape, magnitude, and/or frequency of the spike within the waveform. As illustrated herein, these characteristics will vary for different neurons and different electrodes as a result.

In some implementations, the sampling phase may be performed for one to several minutes. Since neural signals typically have lengths on the order of 1 ms and a repetition rate of 10 neural signals per second, a sampling phase that is 100 seconds long will typically result in the collection of 1,000 neural signals, which can provide statistically significant neural signal characteristics that can be used to construct a reliable template. In some embodiments of the sampling phase, neural signals can be collected until the variation between the average of the received neural signals and the current neural signal decreases below a threshold. In other embodiments, the sampling phase is performed for a predetermined time. In other embodiments, the sampling phase is performed until a predetermined number of neural signals are collected. One of ordinary skill in the art would recognize many variations, modifications, and alternatives.

The one or more characteristics from one electrode may be different from the characteristics associated with other electrodes. This may be due to each electrode measuring different neurons and/or measuring the same neuron from different distances (e.g., based on the position of the probe relative to the neuron and the distance between the electrodes in question). Characteristics associated with different electrodes may include different amplitudes, different shapes, different frequencies, and/or the like. The characteristics may be used to differentiate the signals from each electrode. Sampling the signals from each electrode may also identify characteristics of the electrode such as noise, impedance, or the like. Characteristics of the environment may also be identified such as biological noise, electronic noise, etc.

The characteristics identified during electrode sampling, the characteristics of each electrode, and the characteristics of the environment may be used to assign two or more electrodes to an electrode pool, which can be referred to as a same electrode pool. For example, a first electrode and a second electrode may be selected based on the respective characteristics having a similar amplitude and the electrodes being at least a predetermined distance apart from each other. Examples of characteristics that may be used to assign electrodes to a same electrode pool include, but are not limited to, similar characteristic magnitude (e.g., such as spike amplitude), electrodes with distinct waveforms, distance between electrodes of the electrode pool (e.g., each electrode may be selected based on being at least a predetermined distance from another electrode of the electrode pool), characteristic frequency (e.g., electrodes with signals having differing characteristic frequencies and/or characteristic periods), combinations thereof, or the like. In some embodiments, the magnitude of the signals from two electrodes can different, but both signals can have large amplitudes in absolute terms, e.g. >300 µV. After pooling, which may reduce the signal magnitude, the signals will be large enough to be isolated from noise and sorted as discussed herein.

The electrode, signal, and environment characteristics may indicate how many electrodes may be included in an electrode pool. For instance, an electrode pool may support more electrodes if the electrodes are sufficiently distanced and have distinct waveforms. An electrode pool including electrodes with less distinct waveforms may include fewer electrodes (e.g., to ensure the signals in the resulting pooled signal can be isolated or extracted).

Once the signals from each electrode (or the subset of the electrodes of the probe that are intended to be operated) are sampled, the acquisition phase may be initiated. During the acquisition phase, the switches of the probe may be configured to connect the electrodes assigned to a same electrode pool to a same lead. The receiver may receive a pooled signal from the electrode pool that includes the signals of each electrode of the electrode pool as they are received concurrently. The receiver may process the pooled signal using the characteristics identified during the sampling phase to identify discrete portions of the pooled signal that correspond to each electrode. Thus, the receiver may isolate different temporal portions of the pooled signal and correlate these different temporal portions (e.g., neural signals) with individual electrodes in the pool and ultimately associate them with different neurons.

In some instances, the pooled signals may change over time (e.g., simply as a result of time or as a result of changes in the subject being measured). The electrode pools may be recalibrated to ensure precision in processing of subsequent pooled signals. For example, when characteristics of a pooled signal deviate from expected characteristics (e.g., amplitude, frequency, period, shape, combinations thereof, or the like) by more than a threshold amount, the acquisition phase may be halted and the sampling phase may be performed again. In another example, when a time interval expires (e.g., after 30 minutes, 1 hour, etc.), the acquisition phase may be halted and the sampling phase may be performed again.

During the subsequent sampling phase, the signals from each electrode are sampled again to identify a new characteristic. In some instances, the characteristics of the electrode and/or the environment may also be identified (e.g., which may or may not differ from the previous characteristics of the electrode and/or the environment). The new characteristics may be used to assign electrodes to new electrode pools. Once the subsequent sampling phase is completed, the acquisition phase may be resumed. The sampling phase may be repeated as necessary to ensure the signals received associated with each individual electrode can be isolated from the pooled signal.

FIG. 1 is a diagram illustrating an electrode pooling system according to some aspects of the present disclosure. The electrode pooling system may include receiver unit 104 that receives signals from a probe 108 positioned within a sensing environment. Probe 108 may be configured for use in space-limited environments such as a brain to record electrical signals from neurons. In space-limited environments, the size and shape of the probe may be limited to fit within the environment and to limit impact on the environment itself. Probe 108 may include an electrode array organized into a set of banks including bank 120, bank 130, and bank 140. Each bank includes a set of electrodes. As illustrated in FIG. 1, bank 120 includes electrodes 122, 124, 126, and 128 and bank 130 includes electrodes 132, 134, 136, and 138. Electrodes in bank 140 are not illustrated for purposes of clarity. Although only four electrodes are illustrated for each bank, it will be appreciated that each bank can include fewer or additional electrodes as appropriate to the particular application. In neural sensing applications, probe 108 can include electrodes fabricated as metal pads approximately 10 µm×10 µm and include on the order of 1,000 electrodes mounted on a silicon shank 70 µm in width and 20 µm in thickness (extending into the plane of the figure).

Electrodes 122 and 132 are electrically connected to receiver unit 104 using lead 150, which can also be referred to as a wire or a trace, and switch 123, which corresponds to electrode 122, and switch 133, which corresponds to electrode 132, respectively. For purposes of clarity, the switches connecting the other electrodes to leads 152, 154, and 156 are not labeled, but are illustrated in FIG. 1. Each of the leads including leads 150, 152, 154, and 156 may be configured to convey signals from the electrodes in each bank to receiver unit 104. Display 106 can be used to visualize data collected using probe 108 and receiver unit 104.

In some instances, probe 108 may include fewer leads 150/152/154/156 than electrodes, for example, in applications that are characterized by a space-limited environment such as the brain. For example, the quantity of leads 150/152/154/156 may be approximately equal to the quantity of electrodes in each bank, for example, electrodes 120/124/126/128 in bank 120. As discussed above, probe 108 may include a set of switches that can be independently operated to connect each of the electrodes to one of the leads. In some instances, probe 108 may include a switch for each electrode (e.g., enabling the connection or disconnection of each electrode of the electrode pool). In other instances, probe 108 may include greater or fewer switches than electrodes, thereby enabling more complex switching schemes. The set of switches may be operated to connect zero or more electrodes to the leads at a time. Additional description related to switch architectures is provided in relation to FIGS. 7A-7D.

The switches enable probe 108 to operate in both a sampling phase and an acquisition phase, which can be performed consecutively one or more times. During the sampling phase, the set of switches associated with a lead may be operated sequentially to iteratively connect a single electrode to each lead. Receiver unit 104 may sample signals from the connected electrodes for a time interval. Then, receiver unit 104 may operate the set of switches to disconnect the electrodes that were initially connected and connect new electrodes. This process may iterate over the electrodes until receiver unit 104 has sampled each electrode or a subset of electrodes that are of interest. In some instances, the sampling phase may operate bank-by-bank in which the electrodes in each bank may be sampled concurrently, with each of the electrodes in the bank being connected via a different lead. In other instances, the set of switches may be operated to sample electrodes that are staggered by a predetermined distance from other electrodes that are being sampled at the same time, with each electrode being connected via a different lead.

During the acquisition phase, receiver unit 104 may assign the electrodes to electrode pools. Each electrode pool may include two or more electrodes. Receiver unit 104 may assign each electrode to an electrode pool or only those electrodes that may be of interest (e.g., electrodes positioned near neurons of interest, etc.). Receiver unit 104 may assign electrodes that may be configured to connect to a same lead. For instance, probe 108 as shown is configured to connect one electrode from each bank using a same lead, i.e., bank 120 and bank 130 using lead 150. Receiver unit 104 may operate the set of switches to connect to the electrodes of the electrode pool to receiver unit 104. Receiver unit 104 may then receive a pooled signal from each electrode pool. The pooled signal may correspond to the signals from each electrode of an electrode pool being received concurrently.

Receiver unit 104 may output electrode signals for presentation by display 106 or for processing by computer 107. In the sampling phase, receiver unit 104 may output the signals received from each individual electrode being sampled with an indication as to the electrode from which the signal originated. During the acquisition phase, receiver unit 104 may determine the portion of the pooled signal (or just the characteristics thereof) that corresponds to each electrode of the electrode pool. Receiver unit 104 may output the portion of the pooled signal (or just the characteristics thereof) with an indication as to the corresponding electrode. In some instances, receiver unit 104 may also output the pooled signal for reference or to enable a determination as to when to execute a subsequent sampling phase.

Embodiments of the present invention utilize a method of mapping electrodes to leads including selecting multiple electrodes with suitable signals and connecting them to the same lead. In contrast with conventional multiplexing approaches, which may involve cycling the switches, embodiments of the present invention operate by leaving switches corresponding to the multiple electrodes closed. Accordingly, a "pool" of electrodes is created with signals that are summed and transmitted on the same lead. The pooled signal is processed at a receiver unit to separate individual signals from the pooled signal. Under suitable conditions, embodiments of the present invention record many neurons per lead without an appreciable loss of information. Thus, embodiments of the present invention contrast with conventional approaches that attempt to maintain separation between signals, including systems that highlight low cross-talk between electrodes as a figure of merit.

Though only one probe 108 is depicted, receiver unit 104 may operate any number of probes simultaneously. Each probe may be the same or different from probe 108. Each probe may include an array of electrodes in which each electrode may be independently connected or disconnected using a set of switches that can be operated by receiver unit 104. Receiver unit 104 may output the signals received from the multiple probes via display 124 concurrently with an indication as to which signals correspond to which electrodes within which probes.

Thus, embodiments of the present invention provide a significant improvement in the number of neurons that can be analyzed in a given period of time. For instance, extending the example of probe 108, if a probe containing five banks were utilized, signals from five electrodes could be received concurrently during the acquisition phase, increasing the number of neurons that can be analyzed using a single lead by a factor of five in comparison with conventional techniques. Of course, this is merely an example, and other embodiments will utilize electrode pooling with different switch architectures to achieve different results.

An example probe that can be utilized according to embodiments of the present invention is a Neuropixels probe that includes a single silicon shank with 960 electrodes that can be connected to 384 leads via controllable switches. The electrodes may be divided into three banks (e.g., Bank 0, Bank 1, and Bank 2 oriented from the tip to the base of the shank). Banks 0 and 1 contain a larger quantity of electrodes (e.g., 384 electrodes) than Bank 2 (e.g., 192 electrodes). Each electrode may include a switch that may be operated to connect or disconnect the electrode to a lead. Each lead may be connected to 2 or 3 electrodes at a same relative location within a bank. Although some implementations are described in relation to the Neuropixels probe and banks of electrodes as illustrated in FIG. 2A, embodiments of the present invention are not limited to these particular implementations and a variety of probe structures with or without banks can be utilized as discussed, for example, in relation to FIGS. 7A-7D.

Figure 2A:
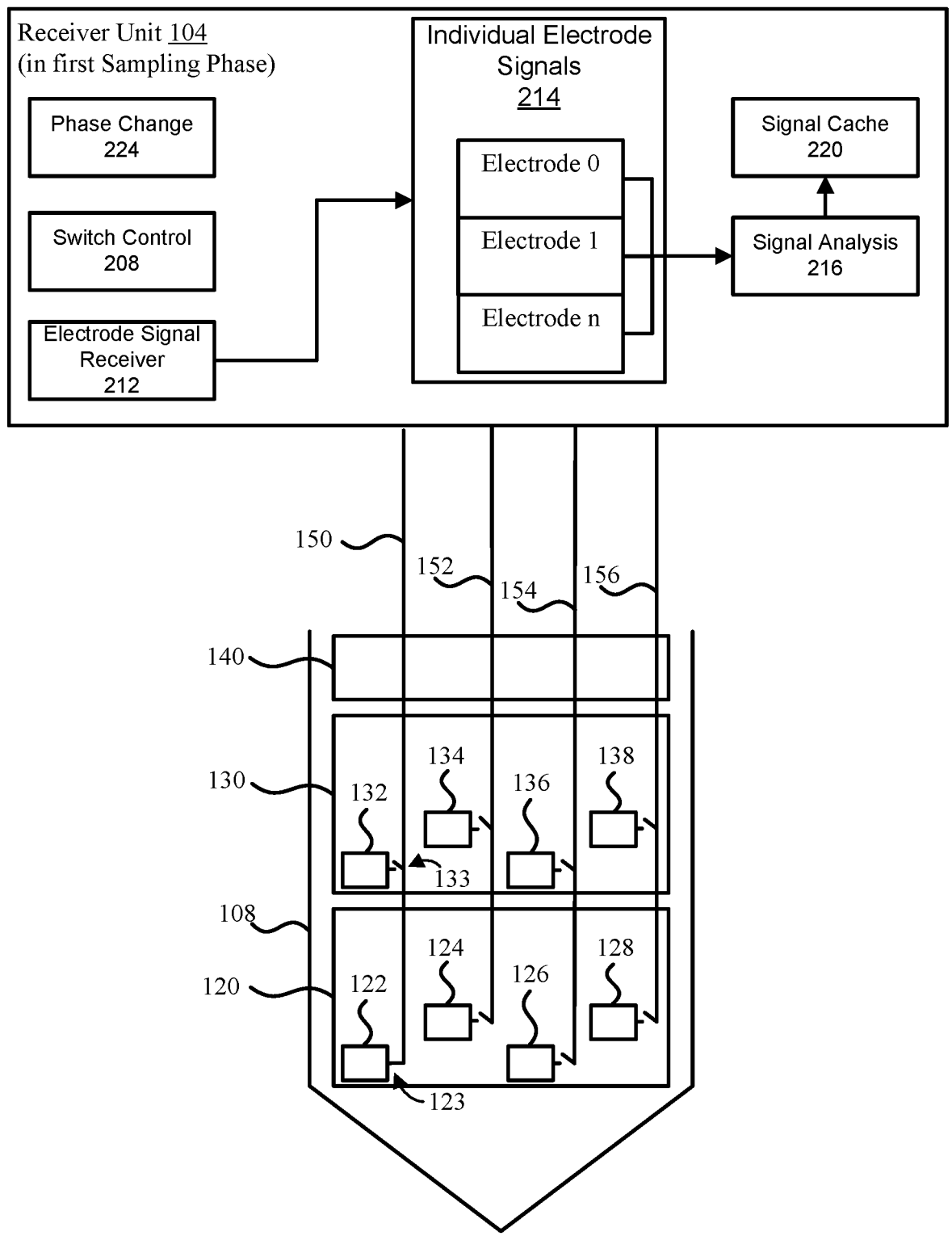
FIG. 2A is a block diagram illustrating an electrode pooling system during a first sampling phase according to some aspects of the present disclosure.

FIG. 2A is a block diagram illustrating an electrode pooling system during a first sampling phase according to some aspects of the present disclosure. During the first sampling phase, receiver unit 104 may sample one electrode per lead at a time to derive characteristics of the signals originating from this electrode. Receiver unit 104 may include switch control 208 that may be used to operate switches 123, 133, and the like within probe 108 to connect or disconnect individual electrodes. Switch control 208 may store addresses of the switches associated with each electrode. Switch control 208 may use the address of a switch to toggle the switch into a connected or disconnected state. For instance, electrode 122 of bank 120 and electrode 132 of bank 130 are configured to connect to lead 150 through switch 123 and switch 133, respectively. Switch control 208 may operate switch 123 for electrode 122 to connect/disconnect electrode 122 to lead 150 and switch 133 for electrode 132 to connect/disconnect electrode 132 from lead 150. Switch control 208 may connect another electrode in bank 120 concurrently with electrode 122, for example, electrode 124 using the switch corresponding to electrode 124 and lead 152. For instance, in the first sampling phase, switch control 208 may connect 122 to lead 150 as illustrated in FIG. 2A as well as electrode 124 to lead 152, electrode 126 to lead 154, and electrode 128 to lead 156 concurrently with the connection of electrode 122 to lead 150.

Signal analysis 216 may isolate the portion of the received signals that corresponds to a neural signal for storage in signal cache 220. Signal analysis may also store the characteristics and/or a representation of the unprocessed signal in association with the isolated neural signal (e.g., as metadata or the like). In some embodiments, electrode signals 214 are passed through signal analysis 216 for storage in signal cache 220, from which they can later be retrieved for processing by signal analysis 216 or other suitable processors. Thus, storage of electrode signals as well as processing of electrode signals, for example, in determining which electrodes are to be selected for inclusion into an electrode pool, are included within the scope of the embodiments described herein.

Figure 2B:
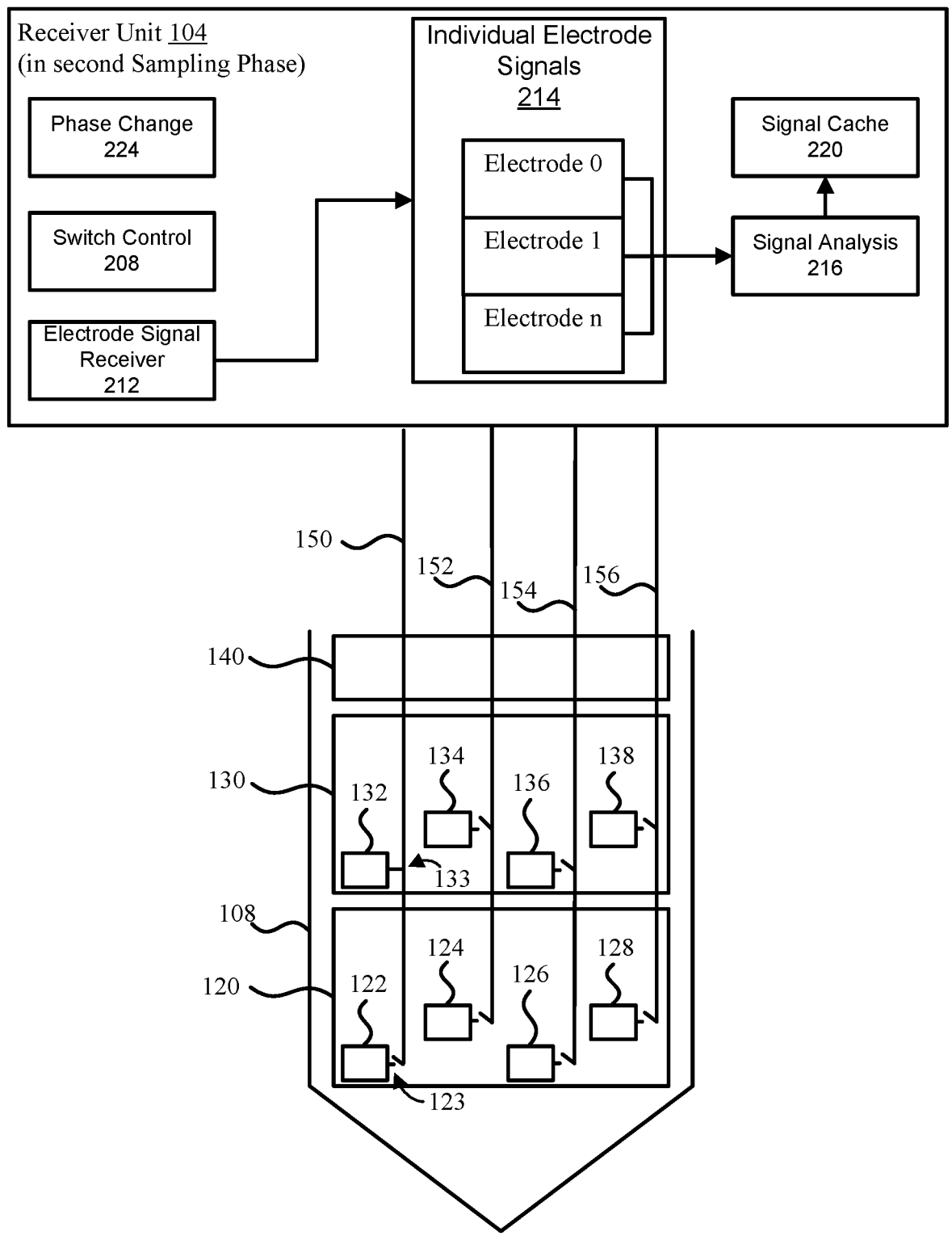
FIG. 2B is a block diagram illustrating an electrode pooling system during a second sampling phase according to some aspects of the present disclosure.

FIG. 2B is a block diagram illustrating an electrode pooling system during a second sampling phase according to some aspects of the present disclosure. In the second sampling phase illustrated in FIG. 2B, switch control 208 has opened switch 123, thereby disconnecting electrode 122 from lead 150 and closed switch 133 to connect electrode 132 to lead 150. In this second sampling phase, characteristics of the neural signals originating from electrode 132 can be analyzed to determine the average shape, average magnitude, average frequency of neural signals, average period between neural signals, or the like. Thus, using this second sampling phase, characteristics associated with electrode 132 are determined. Concurrently, the second sampling phase can obtain information on the characteristics of other electrodes in bank 120 and bank 130. As discussed in relation to FIG. 2A, using the switches corresponding to the various electrodes, switch control 208 may connect electrode 134 to lead 152, electrode 136 to lead 154, and electrode 138 to lead 156 concurrently with the connection of electrode 132 to lead 150.

The process illustrated in FIGS. 2A and 2B can be repeated for additional electrodes present on other banks in order to characterize some or all of the electrodes present on the probe. One of ordinary skill in the art would recognize many variations, modifications, and alternatives.

In some instances, switch control 208 may connect electrodes of a same bank concurrently since each electrode of a bank may be configured to connect to a different lead. For instance, electrode 124 is configured to connect to lead 152, electrode 126 is configured to connect to lead 154, and electrode 128 is configured to connect to lead 156. In those instances, the sampling phase may proceed bank-by-bank connecting each of the electrodes of bank 120, then bank 130, then bank 140, etc. In other instances, switch control 208 may stagger the electrodes that are to be connected concurrently (though still connect the selected electrodes that are configured to connect via different leads). For instance, switch control 208 may connect electrode 122, electrode 134, electrode 126, and electrode 138 concurrently. In still yet another instance, switch control 208 may connect any electrode that has yet to be sampled provided that the electrodes are configured to be connected via separate leads. For example, switch control 208 may use a random number generator or the like to randomly select electrodes for sampling with the constraint that only one electrode per lead may be selected at a time.

Electrode signal receiver 212 of receiver unit 104 may receive signals from connected electrodes over leads 150-156 and provide an indication as to the corresponding electrode that each signal originated from. For instance, electrode signal receiver 212 may provide a representation of signals received from sampled electrodes in individual electrode signals 214. The signals of each electrode may be represented according to an identifier of the electrode. In some instances, the identifier of each electrode may correspond to the address used by switch control 208 to toggle the corresponding switch of the electrode. In other instances, the identifier of each electrode may correspond to a number indicative of the position of the electrode out of all electrodes of probe 108 (or out of electrodes from all probes if additional probes are utilized).

For instance, as depicted in FIG. 2A, receiver 104 organizes the received signals as corresponding from electrode 0, electrode 1, to electrode n, where electrode signal receiver 212 samples signals from n electrodes.

Receiver unit 104 may perform signal analysis on the signals received from each sampled electrode. Signal analysis 216 may determine characteristics of each signal that can be used to identify an electrode. For instance, signal analysis 216 may identify characteristics of the neural signals. Examples of characteristics of a neural signal include, but are not limited to, the average shape, average magnitude, average frequency of neural signals, average period between neural signals, or the like. Signal analysis 216 may isolate the portion of the signals that corresponds to the neural signal for storage in signal cache 220. Signal analysis may also store the characteristics and/or a representation of the unprocessed signal in association with the isolated neural signal (e.g., as metadata or the like).

In some instances, electrodes may be sampled for a predetermined time interval to ensure that sufficient information from each signal can be obtained to identify signals from an electrode as being from that electrode. Signal analysis 216 may process signals from a sampled electrode as the signals are received by electrode signal receiver 212. Once the time interval expires, signal analysis 216 may terminate processing of signals from the sample electrode.

In other instances, signal analysis 216 may evaluate the neural signals and corresponding characteristics to determine if a sufficient quantity of neural signals (or characteristics) have been received to identify signals from that electrode. For instance, signal analysis 216 may use a pattern matching algorithm (e.g., convolution or the like) to determine if the difference between each new neural signal varies from the neural signals already characterized by signal analysis 216 by more than threshold amount. If the new neural signals differ from the previously received neural signals, an average of the previously received neural signals, or the like, by more than the threshold amount, then signal analysis 216 may continue. Otherwise, signal analysis 216 may determine that sampling signals from that electrode can be terminated. Alternatively or additionally, signal analysis 216 may determine an extent to which new characteristics may change the average characteristics (e.g. average neural signal magnitude, average neural signal frequency, etc.) when included in the average. If signal analysis 216 determines that the average is changing by more than a threshold amount, signal analysis 216 may continue processing signals from the sampled electrode. If signal analysis 216 determines the average is not changing by more than the threshold amount, signal analysis 216 may determine that sampling signals from that electrode can be terminated.

Once signal analysis 216 terminates processing of signals from an electrode, switch control 208 may disconnect the currently connected electrodes (e.g., electrode 122) from the lead (e.g., lead 150) and connect the next electrode (e.g., electrode 132) to the lead. Sampling of electrodes may continue until each electrode has been sampled or when selected electrodes have been sampled (e.g., if not all electrodes are to be sampled). When sampling of electrodes is complete, receiver unit 104 may execute phase change 224 to terminate the sampling phase and initiate the acquisition phase.

Figure 2C:
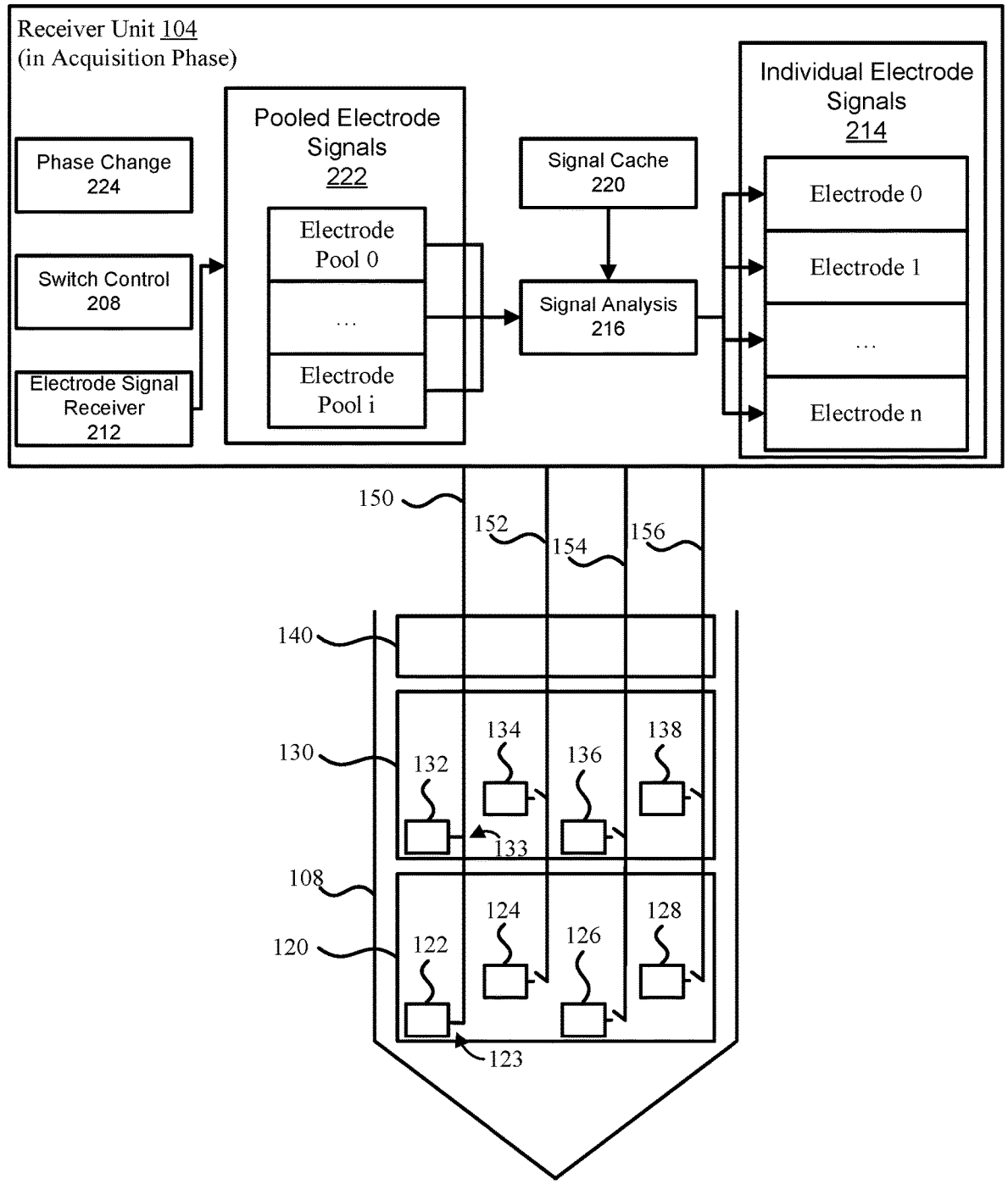
FIG. 2C is a block diagram illustrating an electrode pooling system during an acquisition phase according to some aspects of the present disclosure.

FIG. 2C is a block diagram illustrating an electrode pooling system during an acquisition phase according to some aspects of the present disclosure. The acquisition phase may begin with receiver unit 104 assigning electrodes to electrode pools. Each electrode pool may include two or more electrodes that are connected to receiver unit 104 through a same lead. An electrode may be assigned to electrode pools based on the characteristic of the signals from that electrode. For example, receiver unit 104 may assign an electrode to an electrode pool based on one or more factors such as, but not limited to, that the electrode has a similar neural signal magnitude to electrodes that are assigned to the electrode pool, having a distinct waveform from other electrodes assigned to the electrode pool, being a predetermined distance from other electrodes assigned to the electrode pool, having a neural signal frequency that is greater than a first threshold or less than a second threshold, having a mode that is greater than a third threshold or less than a fourth threshold, combinations thereof, or the like.

Assigning electrodes to an electrode pool may be further based on noise properties of the electrodes.

Receiver unit 104 may use the noise properties of electrodes to determine the number of electrodes to assign to an electrode pool. Electrodes may include multiple sources of noise such as thermal ("Johnson") noise from the impedance of the electrode, biological noise (e.g., also referred to as hash noise) resulting from distant firing neurons, and/or electronic noise from a downstream amplifier, multiplexer, analog-to-digital converter, or the like. Thermal noise at an electrode may be statistically independent (e.g., statically independent of the noise at other electrodes in the electrode pool). Biological noise may be similar across nearby electrodes (e.g., due to nearby electrodes detecting the same distant firing neurons). In some instances, the biological noise can be private to each electrode (e.g., statistically independent of the noise at other electrodes in the electrode pool) when electrodes in the electrode pool are spaced apart.

The private noise of an electrode may be defined as $N_{pri,i} = \sqrt{N_{thermal,i}^2 + N_{bio,i}^2}$, where $N_{pri,i}$ represents the private noise of the $i^{th}$ electrode, $N_{thermal,i}$ represents the electronic noise of the $i^{th}$ electrode, and $N_{bio,i}$ represents the biological noise of the ith electrode. Electronic noise, for example, introduced by a downstream amplifier, multiplexer, analog-to-digital converter, or the like may be represented as $N_{amp}$, which may be common to all of the electrodes of the electrode pool (e.g., $N_{com} = N_{amp}$). In an electrode pool, the private noise may be attenuated by a pooling coefficient $$c_i = \frac{1/Z_i}{\sum_{j=1}^{M} 1/Z_j}$$

(where $Z_i$ represents the impedance of the $i^{th}$ electrode and j represents the quantity of electrodes in the electrode pool) and may be summed up with contribution from other electrodes. The pooled signal may be added to the common noise, which may be statistically independent from other noise sources. The total noise ($N_{tot}$) may be represented as: $N_{tot} = \sqrt{N_{com}^2 + \sum_{i=1}^{M} c_i^2 N_{pri,i}^2}$ or, if electrodes have similar noise and impedance properties as $N_{tot} = \sqrt{N_{com}^2 + N_{pri}^2/M}$.

Determining the size of the electrode pool may be based on the electrodes that are assigned to the electrode pool. The receiver may first sort the isolated neural signals from each electrode to be included in an electrode pool (e.g., from largest $S_{max}$ to smallest $S_{min}$). Receiver unit 104 may identify electrodes that have signals with larger amplitude, which may be easier to identify in the acquisition phase. As electrodes are assigned to the pool, the pooled signal may become so attenuated that the neural signals are no longer sortable from the noise. The size of the electrode pool may be based on the signal-to-noise ratio of neural signals in the pooled signal being larger than that of the smallest sortable neural signals from signals of an electrode $$\left(e.g., = \frac{S_{max}/M}{\sqrt{N_{com}^2 + N_{pri}^2/M}} > \frac{S_{min}}{\sqrt{N_{com}^2 + N_{pri}^2}}\right).$$

The size M of the electrode pool may be represented as $$M = \sqrt{\left(\frac{\beta^2}{2}\right)^2 + (1+\beta^2)\alpha^2} - \frac{\beta^2}{2} - 1,$$

where $\alpha = S_{max}/S_{min}$, $\beta = N_{pri}/N_{com}$.

Thus, the size of the electrode pool may be based on the ratio of private noise to common noise, which may be represented as $\beta = N_{pri}/N_{com}$, and the ratio of largest neural signal amplitude (from signals of the electrodes assigned to the electrode pool) to the smallest neural signal amplitude (representing the threshold amplitude in which a neural signal may be detectable over noise), which may be represented as $\alpha = S_{max}/S_{min}$. The ratio of private noise to common noise and the ratio of largest to smallest useful neural signal amplitudes may vary based on target brain area, recording hardware, how neural signals may be sorted or identified, etc.

If signals from electrodes include a range of neural signals from different neurons, then the pool size, M, may be determined as the value for M that maximizes $$\frac{N_M}{N_1} = \frac{M\left(\alpha - M\sqrt{\frac{1+\beta^2/M}{1+\beta^2}}\right)}{\alpha - 1}.$$

Since the electrode pool size is dependent on the electrodes assigned to an electrode pool, the electrode pools established by receiver unit 104 may not have a uniform size. For instance, some electrode pools may include two electrodes (e.g., when the signals of the electrodes have small neural signal amplitudes), some electrode pools may include four electrodes (e.g., when the signals of the electrodes have a uniform distribution of neural signal amplitudes), some electrode pools may have eight electrodes (e.g., when the signals of the electrodes have large neural signal amplitudes), etc.

For example, electrode 122 and electrode 132 may be assigned to a same electrode pool (e.g., electrode pool 0). Electrode pool 0 may include additional electrodes (not shown) from other banks such as bank 140. Electrodes 116 may not be connected or may be disconnected (as shown) or may be assigned to another electrode pool.

Once the electrodes are assigned to electrode pools, electrode signal receiver 212 may receive a pooled signal from each lead 150-156. In the previous example, electrode signal receiver 212 may receive signals from each electrode in electrode pool 0 (e.g., electrode 122, electrode 132, etc.) concurrently (e.g., as one combined signal). Receiver unit 104 may assign i electrode pools and pooled electrode signals 222 may include a pooled signal from each electrode pool (e.g., for i pooled signals).

The inventors have determined that the benefits of pooling can be quite substantial when electrode pools are assembled in which the individual neural signals have large amplitudes. For example, under conditions of $\alpha$ and $\beta$ that have been encountered, electrode pools with eight electrodes can be formed while still resolving all the signals, thus increasing the neuron/lead ratio by a factor of eight. In another example, if there is a uniform distribution of neural signal amplitudes, an electrode pool with four electrodes increases the neuron/lead ratio by a more modest, but still respectable factor of 2.3 compared to conventional recording.

Signal analysis 216 may process the pooled signal to detect and isolate the neural signals present in the pooled signal. The pooled signal may be a dense signal with more instances of temporal overlap between neural signals than a signal from an individual electrode. Neural signals resulting from temporal overlap may be modeled as an additive superposition of neural signals and noise. By estimating both the spike waveform generated by each electrode (or each neuron) and corresponding spike times, the principal components of the pooled signal can be attributed to the individual electrodes. Thus, signals that have a temporal overlap can be separated based on the characteristics of the signals. In some instances, detecting and isolating neural signals may use a spike sorting algorithm. Spike sorting algorithms group neural signals into clusters based on similarity of shapes. Since signals from a neuron generally have a particular shape, spike sorting may organize neural signals that correspond to a particular neuron. In acquisition phases, spike sorting may be used to identify neural signals that correspond to a same electrode (though the identification of the electrode may be unknown).

Signal analysis 216 may execute the spike sorting algorithm to generate a set of neural signal groups. Each neural signal group may include neural signals that have a same shape, which may correspond to a same electrode. Signal analysis 216 may compare the neural signal groups to the isolated neural signals received during the sampling phase stored in signal cache 220 to identify the electrode from which the neural signals in the neural signal group originated.

In some instances, signal analysis 216 may use data in signal cache 220 to increase the effectiveness of the spike sorting algorithm. The spike sorting algorithm may identify neural signals that are similar from the pooled signal alone (e.g., without prior data from the sampling phase). The spike sorting algorithm may use generic templates (e.g., templates of general neural signal shapes) to determine which neural signals are similar to other neural signals. Furthermore, signal analysis 216 may define custom templates from the neural signals of each electrode received during the sampling phase and use the custom neural signal template during neural signal sorting. For example, the template may be an average of the neural signals associated with an electrode received during a sampling phase. Signal analysis 216 may replace the generic templates used by the spike sorting algorithm with the custom neural signal templates. The spike sorting algorithm may identify more neural signals using the custom neural signal templates then using the generic templates. As an example, using a custom template, the pooled waveform can be analyzed by sliding the custom template across the pooled waveform and extracting neural signals having a shape that is similar to the custom template through this convolution process.

Signal analysis 216 may then output individual electrode signals 214, which may include the isolated neural signals that correspond to a same electrode along with an indication of the electrodes from which the neural signal originated. In some instances, individual electrode signals 214 may also include an identification of the pooled signal, a representation of the pooled signal, a recreation of the signal from each electrode (e.g., the portion of the pooled signal that corresponds to the electrode as recreated from the pooled signal, metadata received during sampling phase, and the isolated neural signals received during the acquisition phase), and/or the like. Individual electrode signals may be presented to a user (e.g., via a display or other output device), transmitted to a remote device, or stored.

During the acquisition phase, receiver unit 104 may compare the isolated neural signals from each electrode received during the sampling phase with the corresponding neural signals received during the acquisition phase to detect drift. Signal drift may occur as a result of probe 108 having moved relative to the object being measured (e.g., the neurons in a brain). If the isolated neural signals from an electrode received during the sampling phase deviate from the corresponding neural signals received during acquisition phase by more than a threshold amount, signal analysis may transmit a communication to phase change 224 to halt the acquisition phase and execute a subsequent sampling phase. During the subsequent sampling phase, new signals may be received from the electrodes and new neural signals may be isolated from the received signal. In some instances, the subsequent sampling phase may only resample those electrodes for which signal drift was detected. In other instances, the subsequent sampling phase may resample all of the electrodes (or a predetermined quantity of electrodes). Signal analysis 216 may replace the isolated neural signals and metadata of each resampled electrode with the new neural signals and new metadata. Once the electrodes are resampled, phase change 224 may terminate the sampling phase and resume the acquisition phase. Accordingly, operation in the sampling phase followed by the acquisition phase may be repeated at periodic intervals, based on changes detected in the neural signals as discussed above, or the like.

Figure 3:
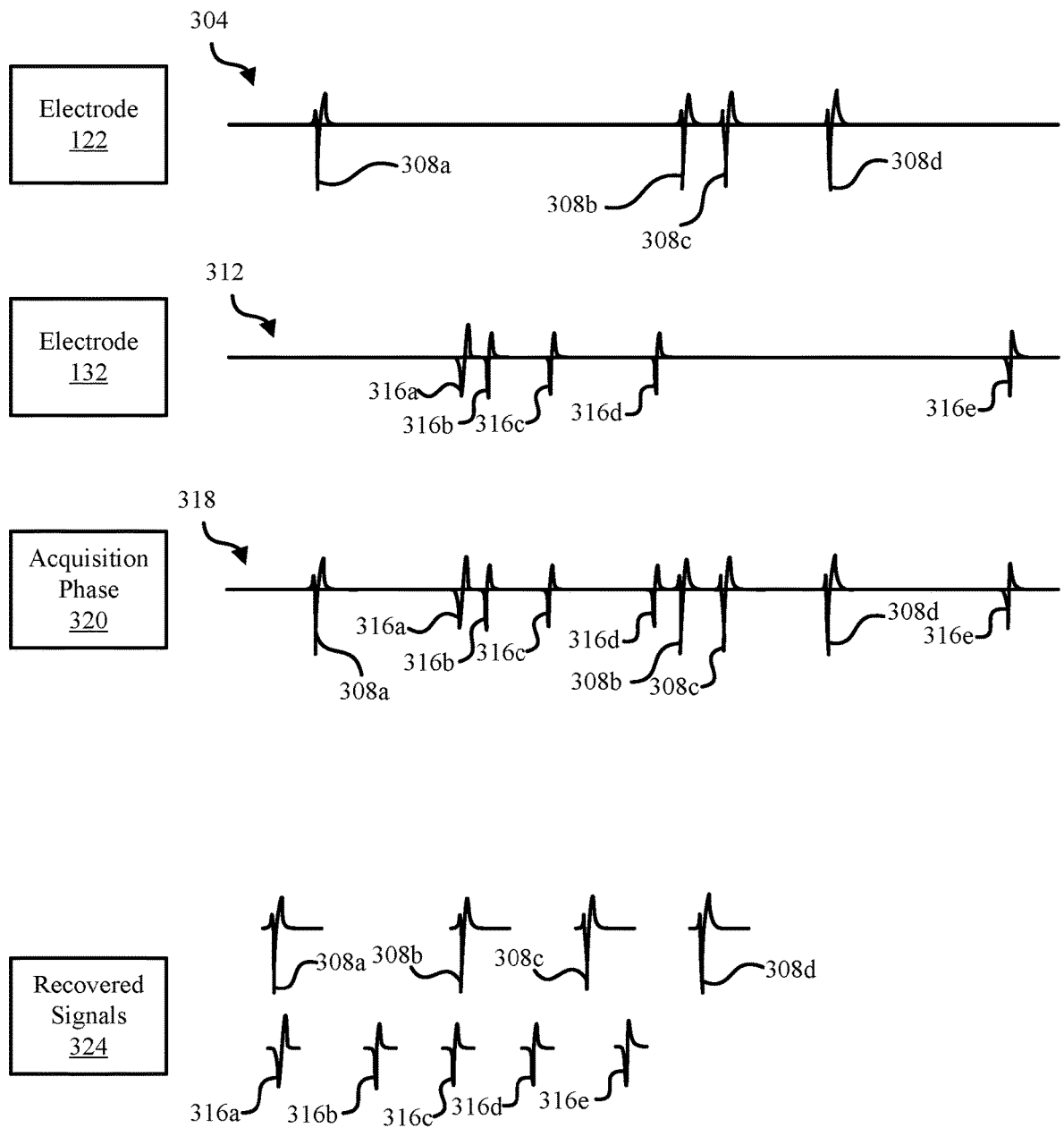
FIG. 3 is a diagram illustrating waveforms and signals measured using an electrode pooling system according to some aspects of the present disclosure.

FIG. 3 is a diagram illustrating waveforms and signals measured using an electrode pooling system according to some aspects of the present disclosure. During a sampling phase, for example, sampling of electrode 122, signals from the electrode may be sampled to identify characteristics of the signals from the electrode. The characteristics may include an isolated representation of the neural signal, a shape of the neural signal, neural signal magnitude or amplitude, frequency of neural signals, period between neural signals, combinations thereof or the like. For instance, waveform 304 is an example waveform that may be received from electrode 122. Waveform 304 may be sampled to detect multiple neural signals 308a-308d that each have similar properties. For instance, each of neural signals 308a-308d include an increasing magnitude to a first peak, followed by a decreasing magnitude to a negative peak, then an increasing magnitude to a higher second peak, and a decreasing magnitude returning to a baseline value. Thus, for electrode 122, each of the neural signals 308a-308d are characterized by a similar shape and temporal profile. As will be evident to one of skill in the art, the shape, amplitude, and other characteristics of the neural signals will be a function of the type of neuron, the shape of the neuron, the orientation of the neuron, the distance between the electrode and the neuron, the material present between the electrode and the neuron, and the like.

Waveform 312 is an example waveform that may be received from electrode 132. Waveform 312 may be sampled to detect neural signals 316a-316e. Each of neural signals 316a-316e include a decreasing magnitude to a first negative peak followed by an increasing magnitude to a positive second peak, and a negative magnitude returning to the baseline value of the signal. Though each of neural signals 316a-316e include the similar identifying properties, the neural signals may vary. For instance, neural signal 316a may have a larger amplitude than neural signal 316c. Since spike sorting and identification are based on the shape of the neural signal (e.g., the properties described above), these minor variations may not affect the isolation of the isolating of the neural signals or the use of the neural signals in identifying a particular electrode from which the neural signals originated. Waveform 304 and waveform 312 may be processed to isolate or extract the neural signals detected in each respective waveform for later use in isolating a pooled electrode.

Once electrode 122 and electrode 132 have been sampled, acquisition phase 320 may be established that includes electrode 122 and electrode 132 connected via a same lead. Signals from electrode 122 and electrode 132 may be received concurrently as a single pooled signal, represented by waveform 318. Waveform 318 may include multiple neural signals with each neural signal being from electrode 122 or electrode 132. The neural signals from waveform 318 may be isolated (e.g., using a wave sorting algorithm, pattern matching, machine-learning, etc.).

Recovered signals 324 represent neural signals recovered from waveform 318 and categorized as being from electrode 122 or electrode 132. Isolated neural signals from waveform 318 may be compared to the isolated neural signals received during the sampling phase (e.g., from waveform 304 and waveform 312). If the shape profile of an isolated neural signal from waveform 318 matches the shape profile of an isolated neural signal from waveform 304, then it can be determined that that neural signal was received from electrode 122. Otherwise, if the shape profile of an isolated neural signal from waveform 318 matches the shape profile of an isolated neural signal from waveform 312, then it can be determined that that neural signal was received from electrode 132.

For instance, a neural signal from waveform 318 having an increasing magnitude to a first peak, followed by a decreasing magnitude to a negative peak, then an increasing magnitude to a higher second peak, and a decreasing magnitude returning to a baseline value may be determined as corresponding to a shape profile of neural signal 308 and resulting from electrode 122. A neural signal from waveform 318 having a decreasing magnitude to a first negative peak followed by an increasing magnitude to a positive second peak, and a negative magnitude returning to the baseline value of the signal may be determined as corresponding to the shape profile of a neural signal 316 and resulting from electrode 132.

Figure 4:
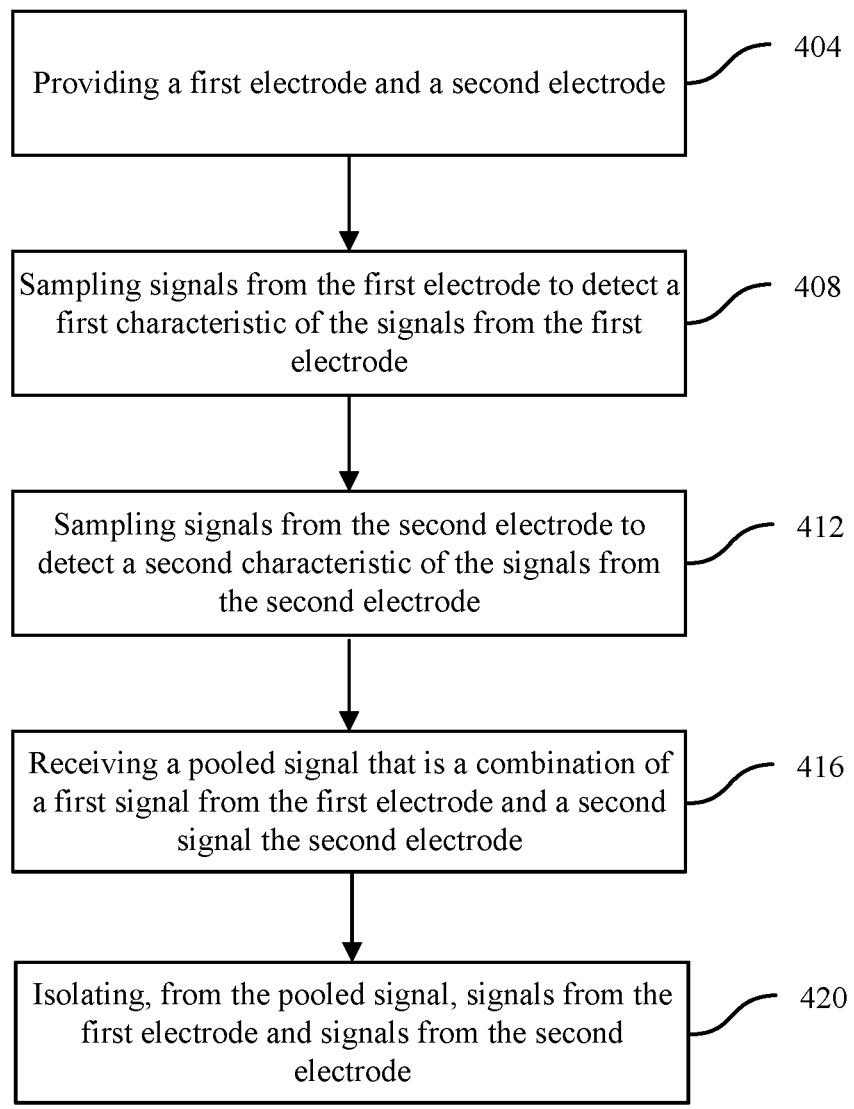
FIG. 4 is a flowchart illustrating an example of a process for operating an electrode pooling system according to some aspects of the present disclosure.

FIG. 4 is a flowchart illustrating an example of a process for operating an electrode pooling system according to some aspects of the present disclosure. The process begins by providing a first electrode and a second electrode (block 404). For example, the first electrode and the second electrode may be included within a probe positioned in a brain. The first electrode and the second electrode may be configured to measure electrical signals from neurons in the brain. The probe also may include one or more additional electrodes. The first electrode and the second electrode may include one or more switches operable to connect or disconnect the first electrode and/or the second electrode to/from a first lead, which may be connected to a receiver unit.

The process continues by sampling signals from the first electrode to detect a first characteristic of the signals from the first electrode (block 408). Signals from the first electrode may be sampled over a first time period while the first electrode is connected to a first lead. During the first time period, the first electrode may be the only electrode connected to the first lead. The first characteristic may correspond to a neural signal (e.g., representing the electrical signal of a neuron firing), a representation of a shape of the neural signal, the magnitude or amplitude of a neural signal, the neural signal frequency, the neural signal period, combinations thereof, or the like.

The process continues by sampling signals from the second electrode to detect a second characteristic of the signals from the second electrode (block 412). Signals from the second electrode may be sampled over a second time period. The switch associated with the second electrode may be operated to disconnect the second electrode from the lead during the first time period. During the second time period, the switch may connect the second electrode to the lead. If the first electrode and the second electrode are configured to connect to a same lead, then the first time period and the second time period may not overlap (e.g., the second time period may begin upon termination of the first time period of vice versa). If additional leads are present, the switches of the first electrode and the second electrode may be operated to connect the first electrode and the second electrode via different leads. In that instance, the first time period may coincide with or overlap with the second time period (e.g., signals may be sampled from both electrodes concurrently provided the electrodes are connected to separate leads).

The second characteristic may correspond to a neural signal, a representation of a shape of the neural signal, the magnitude or amplitude of a neural signal, the neural signal frequency, the neural signal period, combinations thereof, or the like. In some instances, the second characteristic may be of a same type as the first characteristic. For instance, the first characteristic and the second characteristic may both correspond to a shape of a neural signal. In other instances, the second characteristic may correspond to a different type from the first characteristic.

The isolation, from the pooled signal, of the signals from the first electrode and the second electrode can utilize the templates discussed above. As an example, if a first template is formed by averaging signals received from the first electrode during the sampling phase as discussed above, this first template could be compared to discrete portions of the pooled signal, for example, based on the cosine similarity of their waveform vectors, to extract signals associated with the first electrode. Similar processing can isolate signals from the second electrode and other electrodes included in the electrode pool.

The process continues by receiving a pooled signal that is a combination of a first signal from the first electrode and a second signal from the second electrode (block 416). The switches of the first electrode and the second electrode may be operated to connect the first electrode and the second electrode to a same lead at a same time (e.g., as an electrode pool). The pooled signal includes the signals from both the first electrode and the second electrode being received concurrently. For example, the first characteristic detected in the signals from the first electrode and the second characteristic detected in the signals from the second electrode may be present within the pooled electrode.

The process continues by isolating, from the pooled signal, signals from the first electrode and signals from the second electrode (block 420). Isolating the signals from the first and second electrodes may be based on detection of the first characteristics and the second characteristics in signals present in the pooled signal. A spike sorting algorithm may be executed to group the characteristics of the pooled signal that are related into two or more groups. Each group may be compared to the first characteristic detected during sampling the first electrode and the second characteristic detected during sampling the second electrode to determine if the characteristics of the group correspond to the first characteristic or the second characteristic. It may then be determined whether the characteristics of each group were received from the first electrode or the second electrode. Alternatively, the signals from the first electrode and the second electrode may be isolated from the pooled signal based on pattern matching, a machine-learning model (e.g., such as an image classifier, neural network, etc.), image or signal processing, or the like.

It should be appreciated that the specific steps illustrated in FIG. 4 provide a particular method of operating an electrode pooling system according to an embodiment of the present invention. Other sequences of steps may also be performed according to alternative embodiments. For example, alternative embodiments of the present invention may perform the steps outlined above in a different order. Moreover, the individual steps illustrated in FIG. 4 may include multiple sub-steps that may be performed in various sequences as appropriate to the individual step. Furthermore, additional steps may be added or removed depending on the particular applications. Additionally, as described herein, there may be more than two electrodes in the electrode pool. One of ordinary skill in the art would recognize many variations, modifications, and alternatives.

Figure 5:
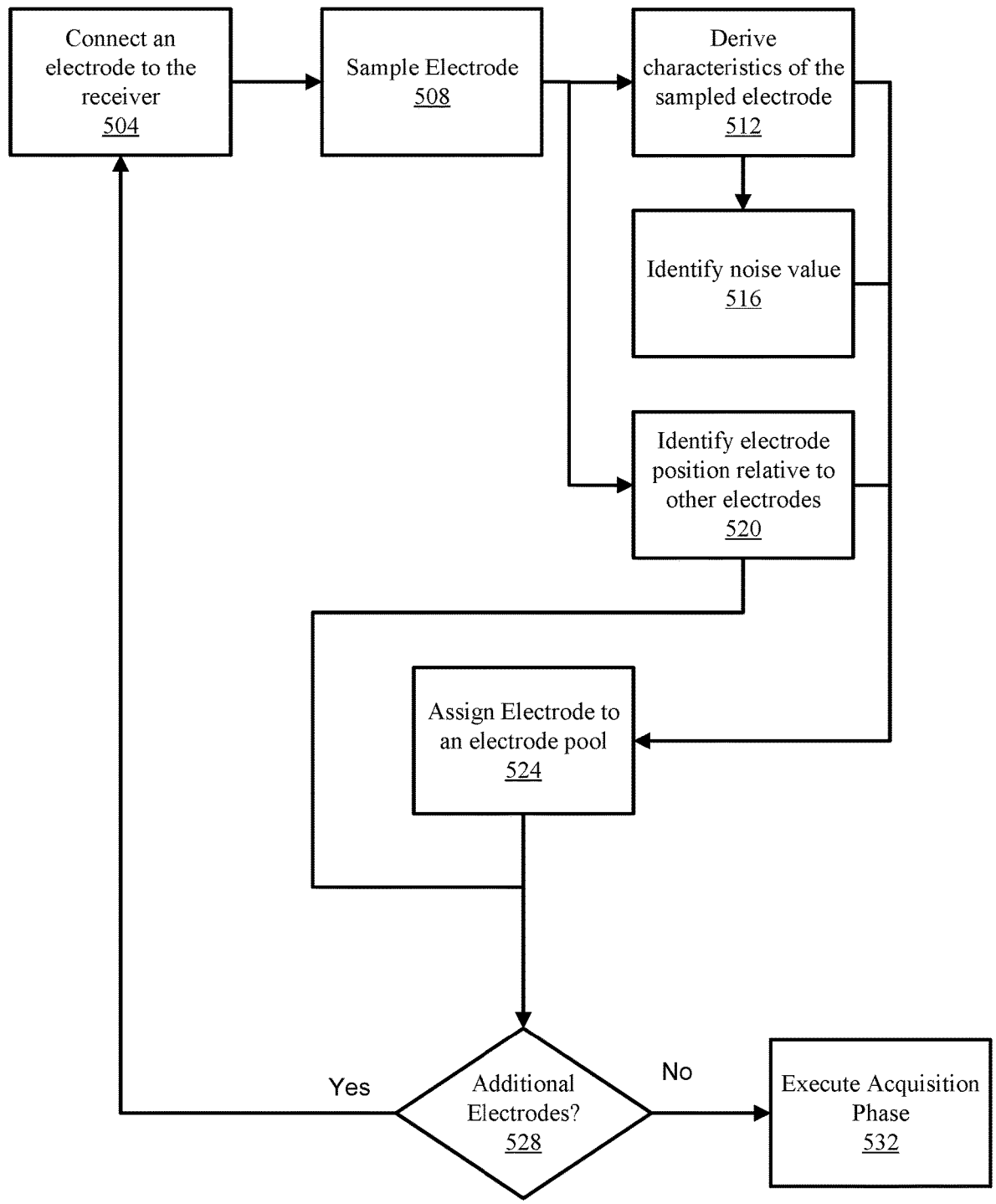
FIG. 5 is a flowchart illustrating a method of selecting electrodes for an electrode pool according to some aspects of the present disclosure.

FIG. 5 is a flowchart illustrating a method of selecting electrodes for an electrode pool according to some aspects of the present disclosure. At block 504, a first electrode may be connected to a receiver via a first lead for a first time period. For example, a switch may be operated to connect the first electrode to the first lead. During the first time period, no other electrodes may be connected via the first lead. But, other electrodes may be connected to the receiver via other leads (if present).

At block 508, signals from the first electrode are sampled. In some instances, sampling signals from the first electrode may include storing the signals received from the first electrode. In other instances, sampling signals from the first electrode may include processing the received signals (e.g., by filtering frequencies to reduce noise, feature detection, etc.) to detect a portion of the signals that are of interest and storing the portion of the signals that are of interest. The signals from the first electrode may be sampled for the entire first time interval. Alternatively, the signals from the first electrode may be sampled until a predetermined quantity (e.g., based on data size, time, or the like) or quality (e.g., based on identified characteristics of the signal) of signals is received.

At block 512, a characteristic of the first electrode may be derived. The characteristic may correspond to a neural signal (e.g., from a neuron firing) in a waveform from the first electrode. Other properties associated with the characteristic may also be derived such as, but not limited to, an amplitude and/or magnitude of the neural signal, a shape of the neural signal, a frequency in which the neural signal occurs, an average period between successive neural signals, combinations thereof, or the like.

At block 516, a noise value of the first electrode may be identified. The noise value may correspond to thermal noise, biological noise, or electrical noise. The noise value may be derived by $\sqrt{N_{thermal,i}^2 + N_{bio,i}^2}$ and $N_{tot} = \sqrt{N_{com}^2 + \Sigma_{i-1}^M c_i^2 N_{pri,i}^2}$. Particular types of noise may be used to determine which electrodes should be included in an electrode pool. For instance, electrodes may be selected so as minimize the likelihood that two electrodes carry a similar biological noise. Biological noise may result from an electrode receiving electrical activity from remote neurons. Electrodes that are physically close to each other may receive the same electrical activity from remote neurons. Electrodes may be selected that are physically far apart from each other to reduce the likelihood that the electrodes may be subject to the same biological noise.

At block 520, a distance of the first electrode relative to other electrodes may be determined, for example, based on the design of the probe. In some instances, it may not be necessary to determine the distance between the first electrode and all other electrodes. For instance, only some of the electrodes may be capable of being connected to a same lead as the first electrode. In those instances, only the distance of the first electrode relative to the electrodes capable of being connected to a same lead may be determined. In other instances (e.g., where multiple switches enable electrodes to connected to different leads, the detected characteristic of the first electrode and other electrodes may be used to identify candidate electrodes (e.g., electrodes that may be selected for inclusion into a same electrode pool as the first electrode). In those instances, only the distance of the first electrode relative to the candidate electrodes may be determined.

At block 524, the first electrode may be assigned to an electrode pool. The electrode pool may include two or more electrodes. In other embodiments, an electrode pool can only include a single electrode, for example, to perform a detailed analysis of signals received from the single electrode. The number of electrodes included in the pool may be based on whether the signals received from the prospective electrodes correspond to a single neuron (e.g., the signal includes large, well-defined spikes) or multiple neurons (e.g., smaller spikes). If the signal of the electrodes corresponds to a single neuron, then the size of the electrode pool may be determined by $$M = \sqrt{\left(\frac{\beta^2}{2}\right)^2 + (1+\beta^2)\alpha^2} - \frac{\beta^2}{2} - 1.$$

If the signal of the electrodes corresponds to multiple neurons, the size of the electrode pool may be determined by the electrode pool size, M, that maximizes $$\frac{N_M}{N_1} = \frac{M\left(\alpha - M\sqrt{\frac{1+\beta^2/M}{1+\beta^2}}\right)}{\alpha - 1}.$$

Electrodes may be assigned to an electrode pool based on one or more factors. Examples of factors include, but are not limited to, the electrode having a similar neural signal magnitude to electrodes that are assigned to the electrode pool, having a distinct waveform from other electrodes assigned to the electrode pool, being a predetermined distance from other electrodes assigned to the electrode pool, having a different biological noise value than other electrodes assigned to the electrode pool, having a neural signal frequency that is greater than a first threshold or less than a second threshold, having a mode that is greater than a third threshold or less than a fourth threshold, combinations thereof, or the like. For example, the derived characteristics from block 512, the noise value from block 516, and the distances from block 520, may be used to assign the first electrode to an electrode pool.

As illustrated in FIG. 5, in some embodiments, the sampling of more than one electrode can be performed prior to assignment of electrodes to electrode pools. Referring to FIG. 5, a flow from block 520 to block 528 is provided. In this flow, multiple electrodes are sampled and the characteristic of each of the plurality of electrodes are derived, the noise value of each of the plurality of electrodes is identified, and the distance of the electrodes relative to other electrodes is determined. Then, after multiple electrodes have been sampled and their parameters analyzed, one or more of the analyzed electrode are assigned to an electrode pool at block 524.

At block 528, it is determined whether there is another electrode to sample. If there are additional electrodes to sample, the process returns to block 504 to sample the next electrode. If all of the electrodes have been sampled, the process continues to block 532 in which the acquisition phase is initiated. As described above, in some embodiments, block 528 is utilized after blocks 512, 516, and 520 when multiple electrodes are sampled before pool assignments are made for the sampled electrodes.

The process illustrated in FIG. 5 assigns electrodes to electrode pools as the electrodes are being sampled (e.g., the first electrode is assigned to an electrode pool before the next electrode is sampled). An alternative process for FIG. 5 may include sampling each electrode and deriving the characteristics of the signals of each electrode, the noise value of each electrode, and the distances of each electrode (e.g., blocks 504-520 may be performed for all electrodes) before assigning electrodes to electrode pools (e.g., block 524).

It should be appreciated that the specific steps illustrated in FIG. 5 provide a particular method of selecting electrodes for an electrode pool according to an embodiment of the present invention. Other sequences of steps may also be performed according to alternative embodiments. For example, alternative embodiments of the present invention may perform the steps outlined above in a different order. Moreover, the individual steps illustrated in FIG. 5 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 6:
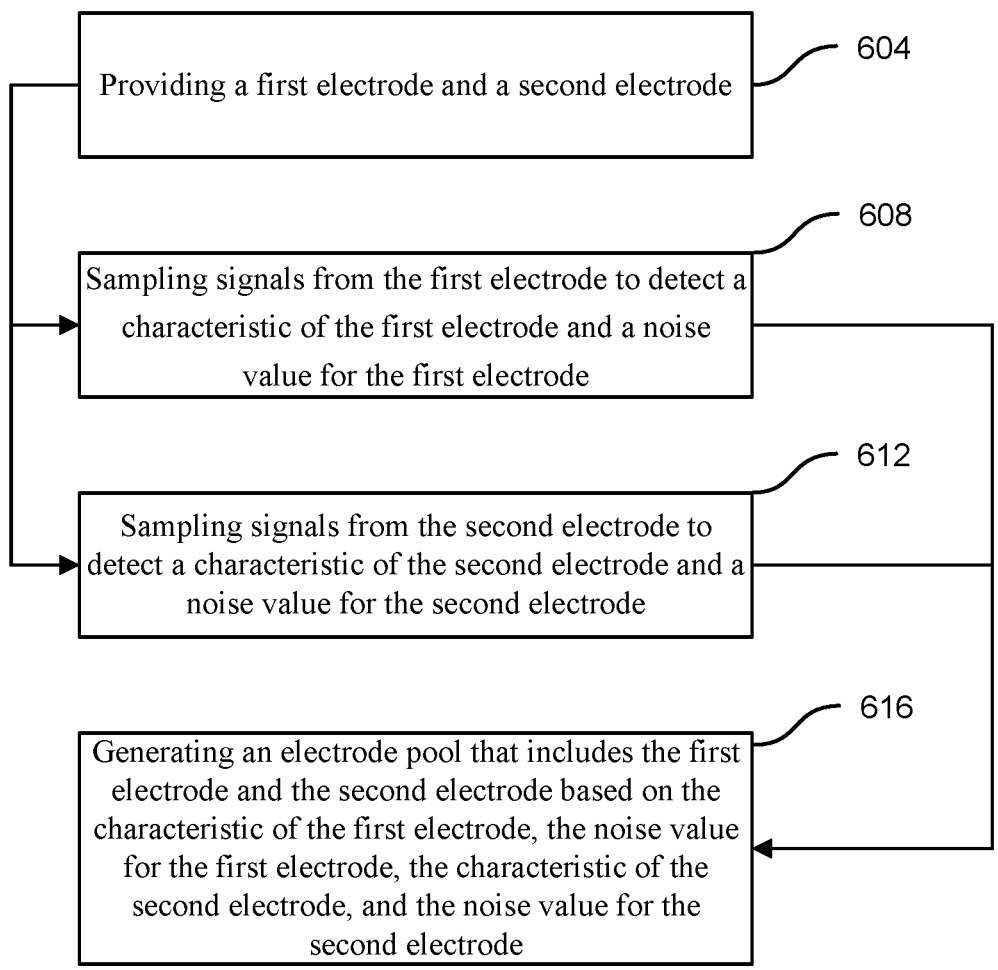
FIG. 6 is a flowchart illustrating an example of a process for generating an electrode pool according to some aspects of the present disclosure.

FIG. 6 is a flowchart illustrating an example of a process for generating an electrode pool according to some aspects of the present disclosure. The process begins by providing a first electrode and a second electrode (604). For example, the first electrode and the second electrode may be included within a probe positioned in a brain. The first electrode and the second electrode may be configured to measure electrical signals from neurons in the brain. The probe also may include one or more additional electrodes. The first electrode and the second electrode may include one or more switches operable to connect or disconnect the first electrode and/or the second electrode to/from a first lead, which may be connected to a receiver unit.

The process continues by sampling signals from the first electrode to detect a characteristic of the first electrode and a noise value for the first electrode (608). Signals from the first electrode may be sampled over a first time period while the electrode is connected to a receiver via a first lead. During the first time period, the first electrode may be the only electrode connected to the first lead. The first characteristic may correspond to a spike (e.g., representing the electrical signal of a neuron firing and represented as a portion of the signal with an absolute magnitude that is greater than a threshold), a representation of a shape of the neural signal, the magnitude or amplitude of a neural signal, the neural signal frequency, the neural signal period, combinations thereof, or the like. The noise value may be derived by $\sqrt{N_{thermal,i}^2 + N_{bio,i}^2}$ and $N_{tot} = \sqrt{N_{com}^2 + \Sigma_{i-1}^{M} c_i^2 N_{pri,i}^2}$.

The process continues by sampling signals from the second electrode to detect a second characteristic of the second electrode and a noise value for the second electrode (612). Signals from the second electrode may be sampled over a second time period while the electrode is connected to the receiver via the first lead. During the second time period, the second electrode may be the only electrode connected to the first lead. The second characteristic may correspond to a spike (e.g., representing the electrical signal of a neuron firing and represented as a portion of the signal with an absolute magnitude that is greater than a threshold), a representation of a shape of the neural signal, the magnitude or amplitude of a neural signal, the neural signal frequency, the neural signal period, combinations thereof, or the like. The noise value may be derived by $\sqrt{N_{thermal,i}^2 + N_{bio,i}^2}$ and $N_{tot} = \sqrt{N_{com}^2 + \Sigma_{i-1}^{M} c_i^2 N_{pri,i}^2}$.

Once signals from the first electrode and the second electrode have been sampled, the process continues by generating an electrode pool that includes the first electrode and the second electrode based on the first characteristic of the first electrode, the noise value for the first electrode, the second characteristic of the second electrode, and the noise value for the second electrode (block 616). For example, the first electrode and the second electrode may be assigned to a same electrode pool based on the first characteristic and the second characteristic having a similar spike magnitude, having a distinct waveform from each other, being a predetermined distance from each other, having a different biological noise value, having a spike frequency that is greater than a first threshold or less than a second threshold, having a mode that is greater than a third threshold or less than a fourth threshold, combinations thereof, or the like. The electrode pool may include one or more additional electrodes that may be selected based on the characteristics of the one or more additional electrodes and the noise value of the one or more additional electrodes.

It should be appreciated that the specific steps illustrated in FIG. 6 provide a particular method of generating an electrode pool according to an embodiment of the present invention. Other sequences of steps may also be performed according to alternative embodiments. For example, alternative embodiments of the present invention may perform the steps outlined above in a different order. Moreover, the individual steps illustrated in FIG. 6 may include multiple sub-steps that may be performed in various sequences as appropriate to the individual step. Furthermore, additional steps may be added or removed depending on the particular applications. One of ordinary skill in the art would recognize many variations, modifications, and alternatives. In particular, although only two electrodes are discussed in relation to FIG. 6, it will be appreciated that more than two electrodes, for example, hundreds or thousands of electrodes, can be sampled, analyzed, and included in electrode pools.

FIGS. 7A-D are diagrams of example switch architectures for electrode pooling systems according to some aspects of the present disclosure. A probe configured to operate in an acquisition phase may include programmable switches that may be operated to connect or disconnect each electrode. The number of switches per electrode may indicate the number of leads that each electrode may be connected to.

Figure 7A:
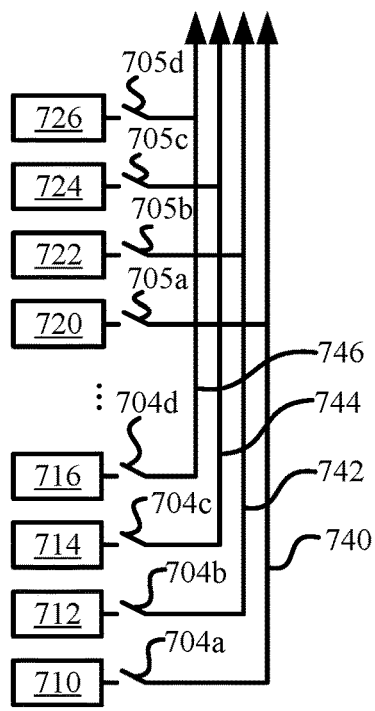
FIGS. 7A-D are diagrams of example switch architectures for electrode pooling systems according to some aspects of the present disclosure.

For instance, FIG. 7A is a diagram of an electrode switching configuration in which each electrode includes one switch (e.g., limiting each electrode to be connected to zero or one leads). A first bank of electrodes includes electrodes 710-716. Each electrode 710-716 may be connected to a respective switch 704a-704d that can connect an electrode to a lead. For instance, electrode 710 may be connected to switch 704a that is configured to connect or disconnect electrode 710 to/from lead 740. Electrode 712 may be connected to switch 704b that is configured to connect or disconnect electrode 712 to lead 742. Electrode 714 may be connected to switch 704c that is configured to connect or disconnect electrode 714 to/from lead 744. Electrode 716 may be connected to switch 704b that is configured to connect or disconnect electrode 716 to/from lead 746.

Electrodes 720-726 may correspond to a second bank of electrodes. Electrodes 720-726 may each include a switch 705a-705d to connect a respective electrode to a lead. For instance, electrode 720 may connect to switch 705a that is configured to connect or disconnect electrode 720 to/from lead 740. Electrode 722 may include switch 705b to selectively connect electrode 722 to lead 742. Electrode 724 may include switch 705c to selectively connect electrode 724 to lead 744. Electrode 726 may include switch 705d to selectively connect electrode 726 to lead 744.

The switches enable two or more electrodes to be connected to a same lead. For instance, during the sampling phase, signals from electrode 710 and electrode 720 may be sampled separately (e.g., only one electrode connected to lead 740 at a time). During the acquisition phase, switch 704a and 705a may connect both electrode 710 and electrode 720 to lead 740 at the same time such that lead 740 may carry the signals of electrode 710 and electrode 720 concurrently. Due to the configuration of the switches, the pooled electrodes may be limited to those electrodes that can be connected to a same lead. For example, a first electrode pool may include electrode 710 and electrode 720, a second electrode pool may include electrode 712 and electrode 722, a third electrode pool may include electrode 714 and electrode 724, and a fourth electrode pool may include electrode 716 and electrode 726.

Figure 7B:
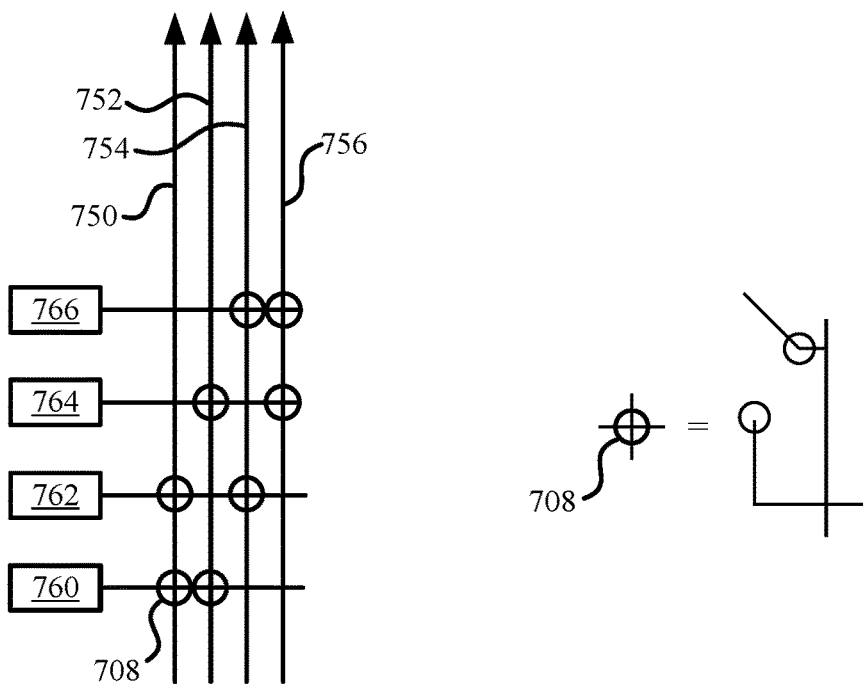

FIG. 7B is a diagram of an alternative switching configuration in which each electrode includes multiple switches per electrode. Each switch 708 can be operated to open or close a circuit that connects an electrode to a lead. Each electrode can be connected to two leads, enabling an increased number of pooling configurations. As illustrated in FIG. 7B, electrode 760 can connect to leads 750 or 752, electrode 762 can connect to leads 750 or 754, electrode 764 can connect to leads 752 or 756, and electrode 766 can connect to leads 754 or 756.

During a sampling phase, switches may be operated so that each electrode is connected to a different lead. In an acquisition phase, an electrode pool may include electrodes 760 and 762 connected to a same lead (e.g., lead 750). Alternatively, electrode pools may be defined using any combination of electrodes (subject to the constraints of assigning electrodes to electrode pools as discussed above). For instance, a first electrode pool may include electrodes 760 and 762 connected to lead 750 and a second electrode pool may include electrodes 764 and 766 connected to lead 756. In some implementations, a switch is provided between every electrode and every lead, i.e., twice the number of switches that are illustrated in FIG. 7B. This switching configuration may be used to form optimal electrode pools since any electrode may be assigned to any electrode pool.

Figure 7C:
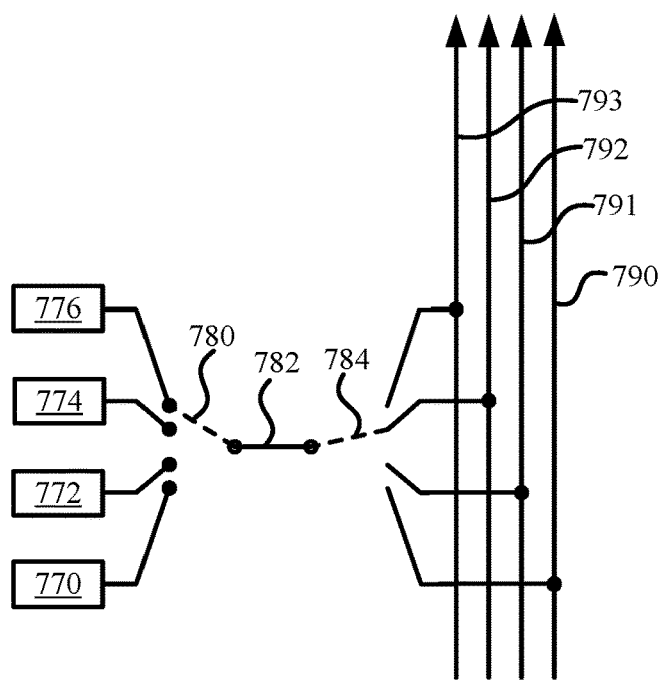

FIG. 7C is a diagram of another alternative switching configuration in which a double switch 782 may be utilized to selectively connect an electrode of electrodes 770-776 to a lead of leads 790-793. Signals from electrodes that are close together may be redundant due to the electrodes proximity to a same neuron being almost the same. To reduce the impact of redundant signals, the double switch enables selection of one electrode per every four electrodes. For instance, electrode 776 may be connected via a first end 780 of double switch 782. The second end 784 of double switch 782 may connect electrode 776 to a particular lead such as lead 793. Double switching may prevent receiving the redundant signals (from adjacent or nearby electrodes) while providing the flexibility of connecting electrodes to any lead.

Figure 7D:
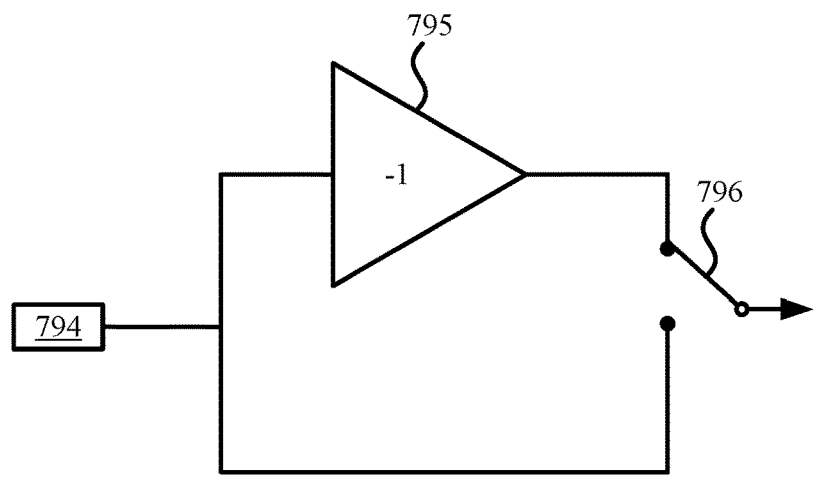

FIG. 7D is a diagram of an inverter that may be operated by a switch to invert signals received from an electrode. For example, inverter 795 may change the sign of the signals received from electrode 794 when switch 976 is open. When switch 796 closes, the inverter is shorted, causing the signal from electrode 794 to be connected to the larger circuit unaltered. The inverter may improve identification of electrodes from a pooled signal. For instance, if half of the electrodes of an electrode pool are inverted, it may be easier to differentiate the spike shapes of the pooled signal. In some instances, extracellular signals from cell bodies may start with a negative voltage swing. Using an inverter in those instances may double the space of waveforms that occur in the pooled signal, which may allow for electrode pools of a greater size. In addition, the inverter may aid the spike sorting algorithm, which may further increase the number of electrodes that can be included in an electrode pool. In some instances, an additional switch (not shown) may be included to enable the electrode to connect to or disconnect from the larger circuit.

A probe, such as probe 108 of FIG. 1, may include any of the switching configurations described in connection to FIG. 7A-D. In some instances, the probe may include one switch configuration. In other instances, the probe may include multiple switching configurations to enable the probe to be configurable for various uses.

Figure 8:
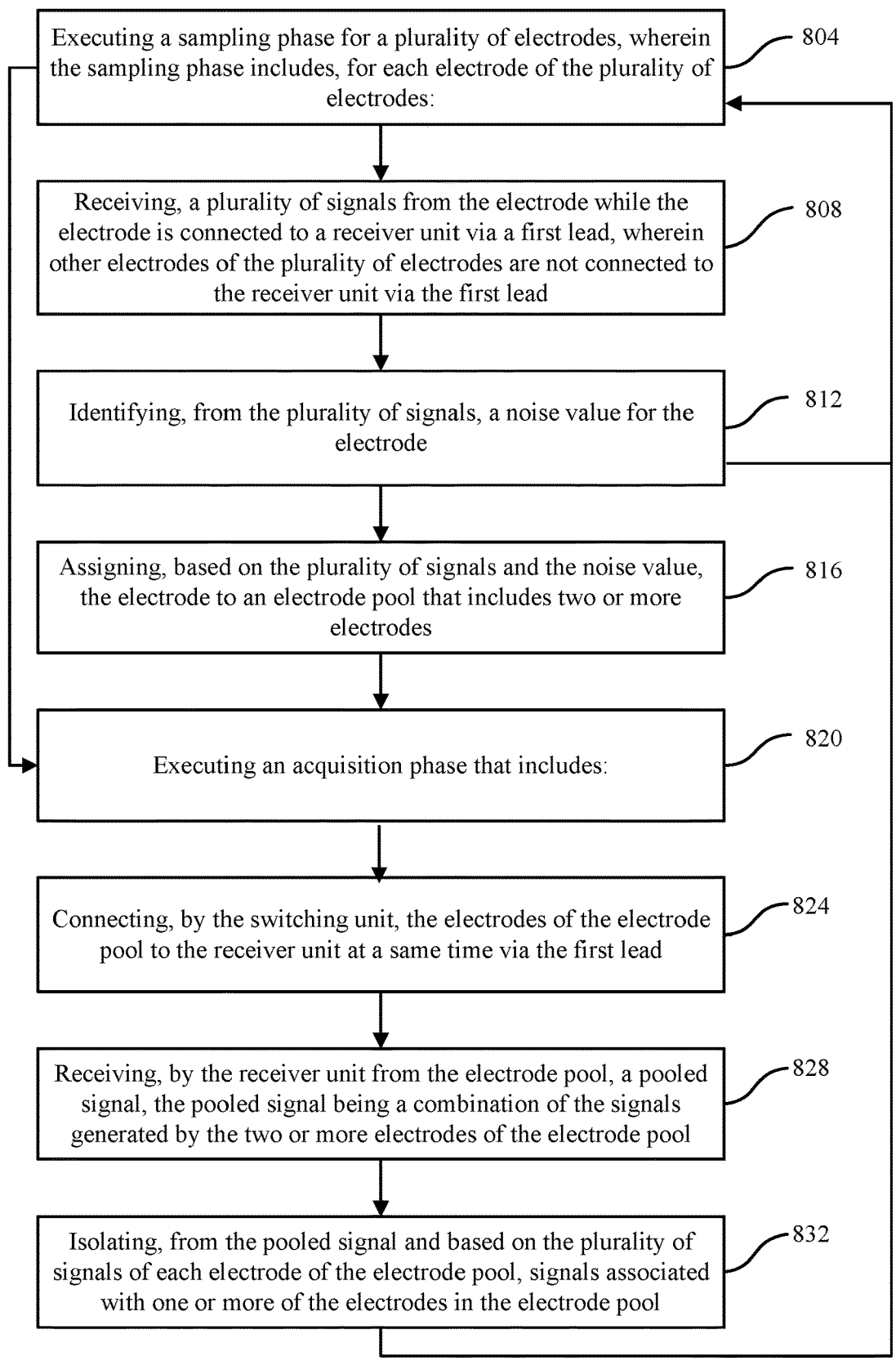
FIG. 8 is a flowchart illustrating an example of a process for operating an electrode pooling system according to some aspects of the present disclosure.

FIG. 8 is a flowchart illustrating an example of a process for operating an electrode pooling system according to some aspects of the present disclosure. The process begins by executing a sampling phase for a plurality of electrodes (block 804). The sampling phase may include, for each electrode of the plurality of electrodes, receiving, a plurality of signals from the electrode while the electrode is connected to a receiver unit via a first lead (block 808). The plurality of signals may be received over a first time period while other electrodes of the plurality of electrodes are not connected to the receiver unit via the first lead. During the sampling phase, each lead may be connected to a single electrode to enable sampling signals from that electrode.

The plurality of signals may be sampled to identify characteristics of the signals received from the electrode. The characteristics may correspond to a neural signal (e.g., representing the electrical signal of a neuron firing and represented as a portion of the signal with an absolute magnitude that is greater than a threshold), a representation of a shape of the neural signal, the magnitude or amplitude of a neural signal, the neural signal frequency, the neural signal period, combinations thereof, or the like.

The process continues by identifying, from the plurality of signals, a noise value for the electrode (block 812). In some instances, the noise value may correspond to a particular type of noise (e.g., biological noise). In other instances, the noise value may correspond to the total noise, which may be derived by $N_{pri,i}^2 = \sqrt{N_{thermal,i}^2 + N_{bio,i}^2}$ and $N_{tot} = \sqrt{N_{com}^2 + \Sigma_{i=1}^{M} c_i^2 N_{pri,i}^2}$.

In some embodiments, noise measurements are made for each electrode during each sampling phase. In other embodiments, the noise value for an electrode can be measured and used in multiple acquisition phases. Thus, the noise statistics, including the noise value can be acquired and then utilized for a different recording session. In some embodiments, the pool selection can utilize the biological noise, for example, to avoid pooling of electrodes that have biological noise that is correlated with other electrodes that are already in the electrode pool.

If there are additional electrodes to sample, the process returns to block 804 in which a plurality of signals may be received from the next electrode.

The process continues by assigning one or more of the electrodes to an electrode pool based on the plurality of signals and the noise value received from each electrode (block 816). For example, the assigning of the electrode to a pool may include determining, from the plurality of signals and the noise value, that the electrode has a similar spike magnitude to electrodes that are assigned to the electrode pool, has a distinct waveform from other electrodes assigned to the electrode pool, is a predetermined distance from other electrodes assigned to the electrode pool, has a different biological noise value than other electrodes assigned to the electrode pool, has a neural signal frequency that is greater than a first threshold or less than a second threshold, has a mode that is greater than a third threshold or less than a fourth threshold, or combinations thereof, or the like.

Once all of the electrodes have been sampled, the process continues by executing an acquisition phase (block 820) that includes: connecting, by the switching unit, the electrodes of the electrode pool to the receiver unit at a same time via the first lead (block 824). A switch may be operated to connect or disconnect the electrodes in the electrode pool to/from the first lead. The switch enables electrodes to be isolated (e.g., being disconnected or being the only electrode connected to the first lead) or pooled (e.g., connected to the first lead as the same time as the other electrodes of the electrode pool).

The process continues by receiving, by the receiver unit, a pooled signal, the pooled signal being a combination of the signals generated by the two or more electrodes of the electrode pool (block 828).

The process continues by isolating, from the pooled signal and based on the plurality of signals of each electrode of the electrode pool, signals associated with one or more of the electrodes in the electrode pool (block 832). Isolating the signals from the electrodes in the electrode pool may include identifying the neural signals within the pooled signal using the determined characteristics and determining from which electrode the neural signal originated. A spike sorting algorithm may be executed to identify and group neural signals having similar shapes. The receiver unit may determine which neural signal groups correspond to which electrode by comparing the shape of the neural signals in a neural signal group to signals received during the sampling phase. The receiver unit may then output the characteristic of each electrode, store the characteristic of each electrode, and/or transmit the characteristic of each electrode to a remote device.

During the acquisition phase, the receiver unit may detect signal drift in any of the electrodes. For instance, the receiver unit may determine if the neural signals from the pooled signal deviate from the neural signals from the plurality of signals by more than a threshold amount. If the neural signals do deviate from the neural signals in the plurality of signals, then signal drift has occurred. The receiver unit may halt the acquisition phase and execute a subsequent sampling phase. During the subsequent sampling phase the electrodes may be resampled. In some instances, all of the electrodes may be resampled. In other instances, the receiver unit may resample only those electrodes for which signal drift was detected. The receiver unit may assign electrodes to new electrode pools based on the resampled signals.

It should be appreciated that the specific steps illustrated in FIG. 8 provide a particular method of operating an electrode pooling system according to an embodiment of the present invention. Other sequences of steps may also be performed according to alternative embodiments. For example, alternative embodiments of the present invention may perform the steps outlined above in a different order. Moreover, the individual steps illustrated in FIG. 8 may include multiple sub-steps that may be performed in various sequences as appropriate to the individual step. Furthermore, additional steps may be added or removed depending on the particular applications. One of ordinary skill in the art would recognize many variations, modifications, and alternatives.

Using embodiments of the present invention, the impedance of the electrode after implantation in the brain can be measured using neural signals collected during the sampling phase and the acquisition phase. For electrodes that are implanted for extended periods of time, for example in brain-machine interfaces, measurement of the impedance can provide insight into changes occurring in the brain tissue over time.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to, portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A method comprising:
   executing, by a receiver unit, a sampling phase for a plurality of electrodes, each electrode of the plurality of electrodes being connected to a switching unit, the switching unit being connected to the receiver unit via a first lead, wherein the switching unit is configured to connect one or more electrodes to the receiver unit via the first lead, wherein the sampling phase includes, for each electrode of the plurality of electrodes:
      receiving, at the receiver unit, a plurality of signals from the electrode while the electrode is connected to the receiver unit via the first lead, wherein other electrodes of the plurality of electrodes are not connected to the receiver unit via the first lead;
      identifying, from the plurality of signals, a noise value for the electrode; and
      assigning, based on the plurality of signals and the noise value, the electrode to an electrode pool that includes two or more electrodes;
   executing, by the receiver unit, an acquisition phase that includes:
      connecting, by the switching unit, the two or more electrodes of the electrode pool to the receiver unit at a same time via the first lead;
      receiving, by the receiver unit from the electrode pool, a pooled signal, the pooled signal being a combination of the signals generated by the two or more electrodes of the electrode pool; and
      isolating, from the pooled signal and based on the plurality of signals of each electrode of the electrode pool, signals associated with one or more of the electrodes in the electrode pool.

2. The method of claim 1, wherein the switching unit includes a plurality of switches, each switch of the plurality of switches being configured to open or close a circuit between an electrode of the plurality of electrodes and the first lead.

3. The method of claim 1, wherein the switching unit includes a plurality of switches, wherein each switch of the plurality of switches is configured to open or close a circuit between two or more electrodes of the plurality of electrodes and two or more leads, wherein the two or more leads include the first lead, and wherein the two or more leads are connected to the receiver unit.

4. The method of claim 1, further comprising:
   determining that a characteristic of an electrode of the electrode pool is greater than a threshold;
   terminating, in response to determining that the characteristic of the electrode of the electrode pool is greater than the threshold, the acquisition phase; and
   re-executing, by the receiver unit, the sampling phase.

5. The method of claim 1, further comprising:
   defining a sampling time interval that represents an amount of time between two sampling phases;
   determining, during the acquisition phase, that the sampling time interval has expired;
   terminating the acquisition phase in response to determining that the sampling time interval has expired; and
   re-executing, by the receiver unit, the sampling phase.

6. The method of claim 1, wherein the noise value represents a biological noise.

7. The method of claim 1, wherein assigning an electrode to the electrode pool is further based on a frequency in which the plurality of signals is greater than a threshold.

8. A method comprising:
   providing a first electrode and a second electrode, each simultaneously connected to a single lead;
   receiving a first plurality of signals from the first electrode during a first period of time;
   receiving a second plurality of signals from the second electrode during a second period of time;
   receiving, at a same time from the first electrode and the second electrode simultaneously connected to the single lead, a pooled signal comprising a third plurality of signals from the first electrode and a fourth plurality of signals from the second electrode; and
   isolating, from the pooled signal, one or more of the third plurality of signals and one or more of the fourth plurality of signals.

9. The method of claim 8, wherein the first plurality of signals comprise a first plurality of neural signals, the second plurality of signals comprise a second plurality of neural signals, and the pooled signal comprises neural signals.

10. The method of claim 8, wherein the first period of time is associated with an average of the first plurality of signals.

11. The method of claim 8, wherein receiving the first plurality of signals from the first electrode is performed prior to receiving the second plurality of signals from the second electrode.

12. The method of claim 8, wherein receiving the pooled signal comprises receiving the third plurality of signals and the fourth plurality of signals concurrently.

13. The method of claim 8, wherein receiving the first plurality of signals from the first electrode, receiving the second plurality of signals from the second electrode, and receiving the pooled signal are performed using the single lead.

14. The method of claim 8, further comprising computing a first characteristic related to the first plurality of signals, wherein isolating one or more of the third plurality of signals is based at least in part on the first characteristic.

15. The method of claim 14, further comprising computing a second characteristic related to the second plurality of signals, wherein isolating one or more of the fourth plurality of signals is based at least in part on the second characteristic.

16. The method of claim 15, further comprising:
   receiving first updated signals from the first electrode;
   computing a third characteristic using the first updated signals;
   receiving second updated signals from the second electrode;
   computing a fourth characteristic using the second updated signals;
   receiving an updated pooled signal from the first electrode and the second electrode; and
   isolating, from the updated pooled signal, an additional third plurality of signals based on the third characteristic and an additional fourth plurality of signals based on the fourth characteristic.

17. The method of claim 16, wherein receiving the first updated signals and receiving the second updated signals are performed after receiving the pooled signal for a predetermined period of time.

18. The method of claim 16, further comprising detecting a variation between the first characteristic and one or more of the third plurality of signals greater than a threshold.

19. A method comprising:
   providing a first electrode and a second electrode, each simultaneously connected to a single lead;
   sampling signals from the first electrode to detect:
      a characteristic of the first electrode; and
      a noise value for the first electrode;
   sampling signals from the second electrode to detect:
      a characteristic of the second electrode; and
      a noise value for the second electrode; and
   generating an electrode pool that includes the first electrode and the second electrode based on the characteristic of the first electrode, the noise value for the first electrode, the characteristic of the second electrode, and the noise value for the second electrode, wherein signals received from the electrode pool correspond to a combination of signals simultaneously received from the first electrode and the second electrode connected to the single lead.

20. The method of claim 19, wherein the noise value represents biological noise.

21. The method of claim 19, wherein generating the electrode pool includes establishing a circuit that connects the first electrode and the second electrode to a receiver using the single lead.

22. The method of claim 19, wherein sampling signals from the first electrode includes:
   establishing a circuit that connects the first electrode to a receiver using the single lead, wherein the second electrode is not included in the circuit.

23. The method of claim 19, wherein sampling signals from the first electrode occurs over a time interval that ends prior to sampling signals from the second electrode.

24. The method of claim 19, wherein generating the electrode pool is further based on a position of the second electrode relative to the first electrode.

25. The method of claim 19, wherein generating the electrode pool includes determining that the noise value of the first electrode is distinct from the noise value of the second electrode.

* * * * *